(12) United States Patent
Chan et al.

(10) Patent No.: US 12,313,581 B2
(45) Date of Patent: May 27, 2025

(54) POSITION INDEPENDENT AND LONG READ RANGE RESONANT SENSOR

(71) Applicant: Iowa State University Research Foundation, Inc., Ames, IA (US)

(72) Inventors: Yee Jher Chan, Ames, IA (US); Adam Russell Carr, Ames, IA (US); Nigel Forest Reuel, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 127 days.

(21) Appl. No.: 17/820,753

(22) Filed: Aug. 18, 2022

(65) Prior Publication Data

US 2023/0075934 A1  Mar. 9, 2023

Related U.S. Application Data

(60) Provisional application No. 63/239,747, filed on Sep. 1, 2021.

(51) Int. Cl.
  *G01N 27/22*   (2006.01)
  *G01N 27/02*   (2006.01)
  *G01N 33/24*   (2006.01)

(52) U.S. Cl.
  CPC ......... *G01N 27/223* (2013.01); *G01N 27/025* (2013.01); *G01N 27/228* (2013.01); *G01N 33/246* (2013.01)

(58) Field of Classification Search
  CPC ... G01N 27/02–025; G01N 27/22–228; G01N 2033/245; G01N 33/246
  USPC .................................................. 324/633–636
  See application file for complete search history.

(56) References Cited

U.S. PATENT DOCUMENTS

| | | | | |
|---|---|---|---|---|
| 6,975,245 | B1 * | 12/2005 | Slater .................. | A01G 25/167 239/63 |
| 7,642,916 | B2 * | 1/2010 | Phipps ............... | G06K 7/10178 235/385 |
| 9,326,728 | B2 * | 5/2016 | Demir .................... | A61B 5/103 |
| 11,228,040 | B2 * | 1/2022 | Eifert .................. | H01M 8/0254 |

(Continued)

FOREIGN PATENT DOCUMENTS

| | | | | |
|---|---|---|---|---|
| JP | 2020181445 | A * | 11/2020 | ............. G06K 19/07 |
| TW | 454042 | U * | 5/2013 | ............... H04B 5/00 |

OTHER PUBLICATIONS

Zhang; Translation of TW-454042-U (Year: 2013).*

(Continued)

*Primary Examiner* — Eman A Alkafawi
*Assistant Examiner* — Rahul Maini
(74) *Attorney, Agent, or Firm* — Schwegman Lundberg & Woessner, P.A.

(57) ABSTRACT

An inductive-capacitive resonant sensor architecture includes an inductively-coupled extender (ICE) that can both increase read range and lessen the effects of reader/sensor misalignment. The ICE can include a first coil configured with respect to a resonant sensor and a second coil separated from the first coil and coupled to the first coil by electrical wires. An external reader can be arranged with respect to the second coil. This architecture can nearly eliminate misalignment issues between the external reader and the resonant sensor. The ICE can be implemented with a closed circuit design. Additional apparatus, systems, and methods are disclosed.

21 Claims, 25 Drawing Sheets

(56) References Cited

U.S. PATENT DOCUMENTS

| | | | |
|---|---|---|---|
| 2008/0143536 A1* | 6/2008 | Camp | G06K 19/07749 |
| | | | 340/572.7 |
| 2011/0025465 A1* | 2/2011 | Danekilde | G06K 7/0008 |
| | | | 307/104 |
| 2012/0135527 A1* | 5/2012 | Bangera | G01N 31/223 |
| | | | 436/3 |
| 2021/0003567 A1* | 1/2021 | Chahal | G01N 27/745 |

OTHER PUBLICATIONS

Karimata; Translation of JP2020181445A (Year: 2020).*
Calvet, Jean-Christophe, et al., "Sensitivity of Passive Microwave Observations to Soil Moisture and Vegetation Water Content: L-Band to W-Band", *IEEE Transactions on Geoscience and Remote Sensing*, 49(4), (Apr. 2011), 1190-1199.

* cited by examiner

POSITION INDEPENDENT AND LONG READ RANGE RESONANT SENSOR

PRIORITY APPLICATION

This application claims priority under 35 U.S.C. 119(e) from U.S. Provisional Application Ser. No. 63/239,747 filed on 1 Sep. 2021, which application is incorporated herein by reference in its entirety.

STATEMENT OF GOVERNMENT SUPPORT

This invention was made with government support under Grant No. IIP1827578 awarded by the National Science Foundation Grant. The government has certain rights in the invention.

FIELD OF THE INVENTION

The invention relates generally to sensors, in particular to technologies related to resonant sensors.

BACKGROUND

Soil moisture content is a critical environmental parameter that is significant to many scientific and commercial fields. It determines the soil's structure, moderates its temperature, serves as a transport medium for chemicals, and provides the means for life to grow. Soil moisture content is a key parameter in weather and climate models, closing the energy and mass balances due to evapotranspiration processes between land and atmosphere. Geotechnical engineering uses soil moisture content during shrink-swell and strength tests of cohesive soils to ensure the soil has proper mechanical properties before constructing infrastructure on it. Measuring soil moisture content is also extremely important to agriculture and crop management. In particular, measuring soil moisture content determines the field capacity of soil, which is the water retained in soil after being saturated and allowed to freely drain. Known field capacity is critical to monitor to avoid the permanent wilting point of a crop, where the moisture content drops below a point where the plant is capable of recovering.

Continuous monitoring of soil moisture content, or periodic monitoring with acceptable periods, rather than sporadic measurements, is necessary to update climate models and improve crop management practices. It is also advantageous to obtain measurements at multiple depths. Field capacity changes with root depth relative to the water table, which also varies throughout the growing season. Continuous soil moisture monitoring can help prevent crop failure. It can inform real-time dosing of additional irrigation volume, avoiding situations of under and over watering, thereby improving the economics and sustainability of field management practices.

BRIEF DESCRIPTION OF THE FIGURES

The drawings illustrate generally, by way of example, but not by way of limitation, various embodiments discussed in the present document.

DETAILED DESCRIPTION

Figure 1A:
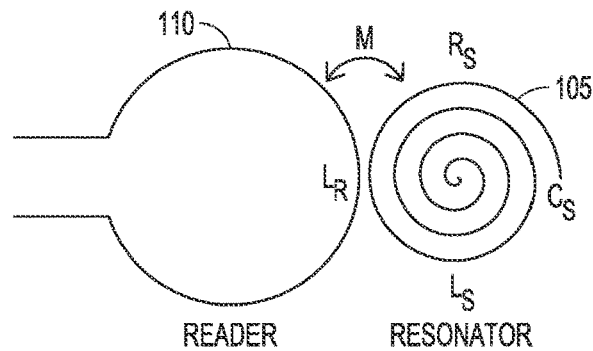
FIGS. 1A-1B are schematics and equivalent circuit model of a conventional wireless resonant sensor system, in accordance with various embodiments.

The following detailed description refers to the accompanying drawings that show, by way of illustration, various embodiments of the invention. These embodiments are described in sufficient detail to enable those of ordinary skill in the art to practice these and other embodiments. Other embodiments may be utilized, and structural, logical, mechanical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Current methods to monitor soil moisture content include remote and in situ methods. Remote methods include microwave remote sensors, e.g., radiometers and ground penetrating radar, which have been used to determine soil moisture content at surface level and near-surface (0-5 cm) level. This is especially useful in meteorological applications and climate models as the near-surface region is the most dynamic region in terms of soil moisture content. Hydrological models can be implemented to extrapolate the soil moisture content to the root zone (>1 m depth) from near-surface measurements. However, truth data from in situ sensors need to be deployed to validate the accuracy of such models.

There are several in situ sensors that can be implemented, including time domain reflectometry, frequency domain reflectometry, capacitive, and resistive. All of these are electromagnetic based sensors. The first three of which measure the relative permittivity of the soil, which changes with soil moisture content. For example, the relative permittivity of water and bulk soil is approximately 80 and 3, respectively. Resistive sensors tend to be more susceptible to electrolytic corrosion and soil ion concentration and are therefore not used in long term deployments. These and other in situ sensors have provided truth data that feed into and validate climate and hydrological models, especially through the widespread work of the International Soil Moisture Network and North American Soil Moisture Database. There are limitations of the currently implemented in situ sensors. All of these previously discussed sensors are active and require a connection to a permanent power supply. The individual price point per sensor and need for centralized data acquisition and power hubs limit the number of measurement nodes that can be deployed; these are typically focused on few measurement sites and do not allow for monitoring heterogenous soil moisture content throughout the field.

Inductive-capacitive (LC) resonant sensors provide an alternative approach for monitoring soil moisture content. LC resonators include an inductor and a capacitor (either discrete or parasitic), which resonate at a specific frequency. This frequency is influenced by changes in the relative permittivity of their surrounding environment giving them the same working principle as other currently used soil moisture sensors. For example, LC sensors have been used to monitor aqueous samples with volumetric moisture changes. Key benefits of resonant sensors are their ultra-low cost point enabled by facile fabrication methods, such as screen printing with no pick and place of integrated circuits, and no on-board battery or wireless power transfer circuitry (e.g., rectifier and capacitor). This allows these resonant sensors to be deployed in many locations, providing holistic measurement of a heterogenous environment. They can be wirelessly and passively activated through non-metallic materials by an interrogation reader, i.e., they do not require a tethered power supply or data connection to read moisture content under the soil. There are two issues of current LC resonant sensors that limit their widespread use in many applications. First, their read range is limited to a short distance (<5 cm), and second, their signal is sensitive to misalignments between the wireless reader and the LC-resonator. To date, stationary and close reader placement during measurement has been required to help mitigate these limitations.

Attempts have been made to overcome these limitations. The read range can be increased through the use of repeater frequency coils, increased quality factors, and increased inductive element size. These can improve read range through free medium like air but are not as effective in lossy systems like wet soil. Sensitivity to misalignment can be overcome through the use of novel reader architectures and interpolating the position of reader/sensor alignment with an array of LC resonators. To this point, however, no attempt has been made to both increase the read range and mitigate misalignment issues in the same reader-sensor architecture.

In various embodiments, a novel LC-resonant sensor architecture including an inductively-coupled extender (ICE) can both increase read range and lessen the effects of reader/sensor misalignment. The ICE can be configured to remain in a fixed position relative to the LC sensor. This architecture nearly eliminates the misalignment issues between the external reader and the LC-resonator. The ICE can be implemented with a closed circuit design, which also enables a robust signal to be realized in a lossy soil substrate even at a depth of one meter. In the design of an ICE embodiment, the feasibility of an ICE-LC sensor architecture was validated through a physical model in Matlab® using an equivalent lumped-element circuit model. Then, an initial prototype was tested using soil samples with varying soil moisture contents. The LC-resonant sensor response was then optimized via changes in ICE coil geometry. The optimized ICE-LC sensor was tested in cyclic soil dehydration experiments to demonstrate correlation of resonant frequency to soil moisture content measured by established wired sensors and reversibility of the response. A smaller, planar form factor of the ICE-LC was tested to demonstrate the ability to maintain diminished misalignment sensitivity without the need for extended read range. All soil moisture content experiments were benchmarked against a capacitive soil moisture sensor.

Figure 1B:
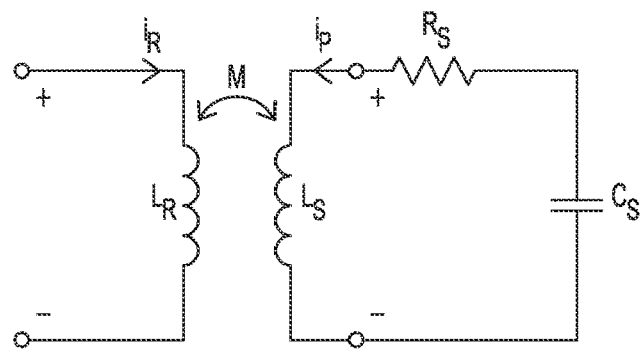

Consider the design and modeling of an ICE-LC coupled circuit. A resonant sensor system consists of an LC sensor and a wireless reader used to interrogate the sensor to determine resonant frequency. The reader supplies an oscillating voltage to a readout coil that inductively couples with the sensor. FIG. 1A is a schematic of a conventional wireless resonant sensor system arranged as a LC sensing system with a reader having a reader coil 110 and a resonator having a sensor coil 105. FIG. 1B is an equivalent circuit model of the LC sensing system of FIG. 1A. The impedance at the readout coil 110 can be expressed as $$Z_1 = j\omega L_r + \frac{\omega^2 M^2}{R_s + j\omega L_s + \frac{1}{j\omega C_s}} \quad (1)$$

where $L_r$, $L_s$, $C_s$, and $R_s$, and M are inductance of the reader coil 110, inductance of the sensor coil 105, capacitance of the resonator associated with the sensor coil 105, resistance associated with the sensor coil 105, and mutual inductance between the reader coil 110 and the sensor coil 105, respectively, as shown in FIG. 1A. The mutual inductance M is expressed as $$M = k\sqrt{L_r L_s} \quad (2)$$

where k is a coupling coefficient between the coupled inductors and has a value in the range $0 \leq k \leq 1$. According to Equation 1, the real part of the impedance will have a maximum at the resonant frequency, which is defined as $$f_0 = \frac{1}{2\pi\sqrt{L_s C_s}}. \quad (3)$$

A network analyzer, such as a standard vector network analyzer (VNA), can be used to measure signals in terms of scattering parameters. The scattering parameters include parameters for reflected signal, $S_{11}$, transmitted signal, $S_{21}$, and reverse parameters, $S_{22}$ and $S_{12}$. When the sensor is brought in proximity to the readout coil, the impedance begins to match, power is transferred to the LC tank, and a minimum is observed in reflected power, which can be measured via the $|S_{11}|$ scattering parameter magnitude. Although the frequency at this minimum does not directly reflect the exact resonant frequency of the sensor due to the imaginary components of the impedance, they are still correlated. This convenient measure can be used to represent the sensor's resonant frequency. Since $C_s$ is a function of relative permittivity of environment, the variation in soil moisture level around the sensor affects the resonant frequency. However, in practice, the resonant frequency is also dependent on the mutual position between the reader and the sensor, detailed below. Magnetic coupling in the typical arrangement of FIG. 1A requires the reader to be in close proximity with the sensor (<5 cm for typical VNA power), limiting the interrogation range of the sensor. Furthermore, fertilizer and minerals present in ground water create a lossy system, which further reduces the power transferred to the LC tank and thereby reduces the interrogation range of the sensor.

Figure 1C:
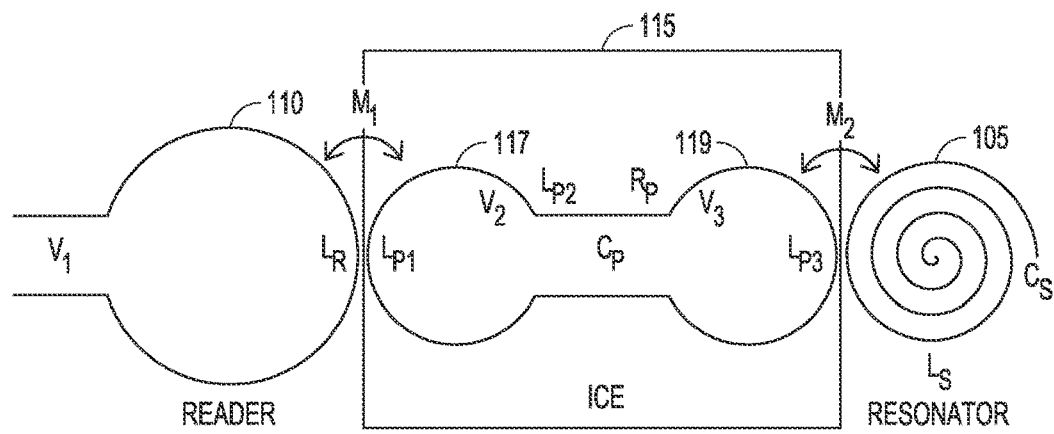
FIGS. 1C-1D are schematics and equivalent circuit model of an example sensor system with inductively coupled extender implemented, in accordance with various embodiments.
Figure 1D:
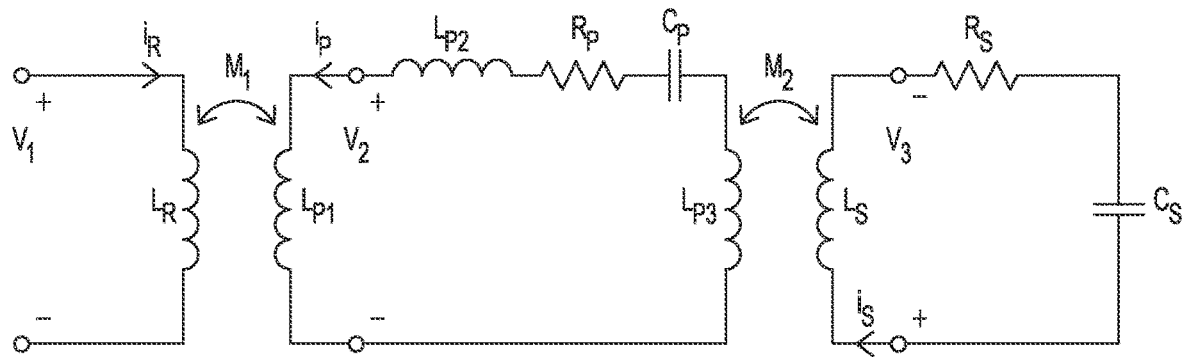

In various embodiments, to overcome these positional and step-off distance limitations of direct, inductive coupling between a reader and a hookup coil, an additional circuit component can be added. An ICE comprising two linked coils used for wireless power transmission can be positioned between a reader coil and a coil of a resonant sensor. FIG. 1C is a schematic showing an ICE 115 between the reader of FIG. 1A having a reader coil 110 and the resonator of FIG. 1A having a sensor coil 105. FIG. 1D is an equivalent circuit model of the LC sensing system with ICE of FIG. 1C. This arrangement can be viewed as being analogous to a repeater that is used to extend read range in previous work, except the coils in the ICE structure of FIG. 1C are wired together in a closed circuit, shown as a dumbbell shape in FIG. 1C, to reduce power loss to the environment. One of the coils, ICE top coil 117, of the ICE 115 receives power from the reader coil 110, whereas the other one of the coils, ICE bottom coil 119, of the ICE 115 interrogates the sensor coil 105 like a conventional reader. In this manner, in a soil moisture monitoring application for example, the ICE top coil 117 can be placed at the soil surface allowing for efficient inductive coupling with the reader coil 110 swept at the surface and the ICE bottom coil can be placed at any level below the ground to the extent that sufficient power can be transferred to the sensor coil 105. Also, because the relative positions of the buried ICE bottom coil 119 and the LC sensor coil 105 are held constant, the parasitic capacitances between these coils are constant and the issue of positional-dependent signal can be mitigated.

FIG. 1D models the circuit of FIG. 1C to show the expected sensor response. Using Kirchhoff's voltage law, the voltages across the points defined in FIG. 1D can be represented as $$V_1 = j\omega L_r i_r + j\omega M_1 i_p \quad (4)$$

$$V_2 = \quad (5)$$
$$j\omega L_{p1} i_p + j\omega M_1 i_r = -j\omega L_{p2} i_p - \frac{i_p}{j\omega C_p} - R_p i_p - j\omega L_{p3} i_p - j\omega M_2 i_s$$

$$V_3 = j\omega L_s i_s + j\omega M_2 i_p = -R_s i_s - \frac{i_s}{j\omega C_s} \quad (6)$$

where the mutual inductances are $$M_1 = k_1 \sqrt{L_r L_{p1}} \quad (7)$$

$$M_2 = k_2 \sqrt{L_{p3} L_s} \quad (8)$$

with $L_{p1}$, $L_{p3}$, $M_1$, $M_2$, $k_1$, and $k_2$ being inductance of the top coil 117, inductance of the bottom coil 1119, mutual inductance between the read coil 110 and the top coil 117, mutual inductance between the bottom coil 119 and the sensor coil 115, a coupling coefficient between the read coil 110 and the top coil 117, and a coupling coefficient between the bottom coil 119 and the sensor coil 115, respectively, as shown in FIG. 1C. The coupling coefficients $k_1$ and $k_2$ have values in the range $0 \leq k_1 \leq 1$ and $0 \leq k_2 \leq 1$, respectively. The variable $L_{p2}$ and $R_p$ represents the inductance and resistance, respectively, of the connecting wires between the two coils, top coil 117 and bottom coil 119, whereas $C_p$ represents the equivalent capacitance for the ICE system. The impedance at the terminals of the readout coil 110 is then expressed as $$Z = j\omega L_r + \frac{\omega^2 M_1^2}{R_p + j\omega(L_{p1} + L_{p2} + L_{p3}) + \frac{1}{j\omega C_p} + Z_s} \quad (9)$$

$$Z_s = \frac{\omega^2 M_2^2}{R_s + j\omega L_s + \frac{1}{j\omega C_s}} \quad (10)$$

Comparing Equations 1 and 9, similarities are noted and the information from the sensor for the modified system of Equation 10 is now used in Equation 9. The magnitude of IS 11 resulting from Equations 1 and 9 can then be modeled using a numerical computation package such as but not limited to Matlab®. For example, the equivalent circuit model provided by the lumped element circuit model of FIG. 1D was analyzed and plotted using Matlab®. Circuit models with additional parallel RLC elements were simulated, using Advanced Design System, to elucidate additional dips observed across the frequency window in practice. To test the response of this system, parameter values that keep resonant frequency in the expected 50 to 200 MHz range were used. Table 1 shows parameters used in the analytical model.

TABLE 1

| Variables | Equation 1 | Equation 9 |
| --- | --- | --- |
| $L_r$ (µH) | 0.3 | 0.3 |
| $L_s$ (µH) | 2.1 | 1 |
| $L_{p1}$, $L_{p2}$ (µH) | — | 1 |

TABLE 1-continued

| Variables | Equation 1 | Equation 9 |
|---|---|---|
| $L_{p3}$ (μH) | — | 0.1 |
| $C_s$ (pF) | 1 | 1 |
| $C_p$ (pF) | — | 1 |
| $R_s$ (Ω) | 3 | 0.5 |
| $R_p$ (Ω) | — | 3 |
| k | 0.2 | — |
| $k_1, k_2$ | — | 0.2 |

Figure 2:
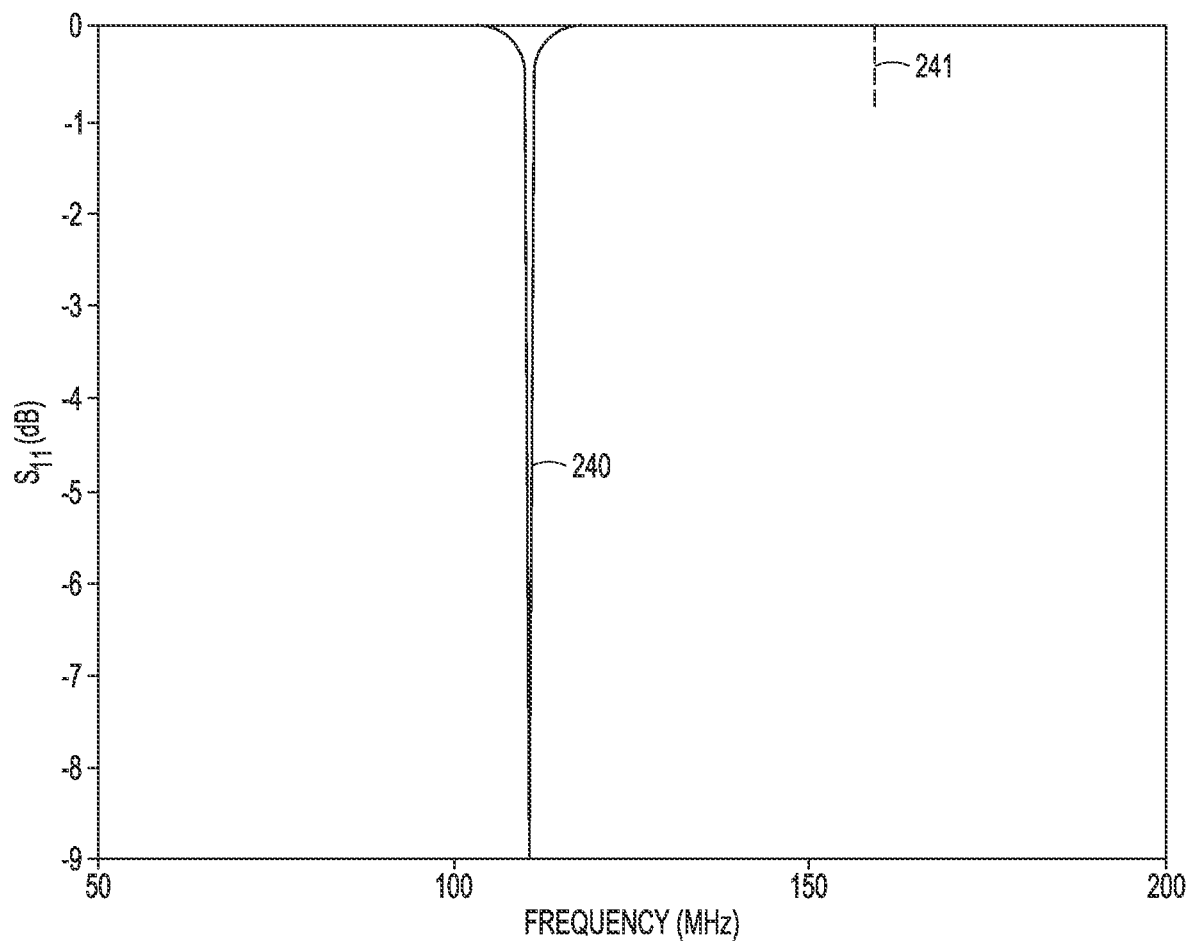
FIG. 2 is a plot of the scattering parameter $S_{11}$ versus frequency for analytical models of an extender with and without a sensor, in accordance with various embodiments.

FIG. 2 is a plot of the scattering parameter $S_{11}$ versus frequency for analytical models of an extender with and without the sensor. Without sensor, there is a signal dip 240. Note that Equation 9 exhibits an additional signal dip 241 at approximately 160 MHz that corresponds to the $Z_s$ term for the coupled sensor coil. In the presence of the sensor, the dip 241 observed at around 160 MHz has negligible effect on the main dip 240 from the ICE extender system.

Figure 3A:
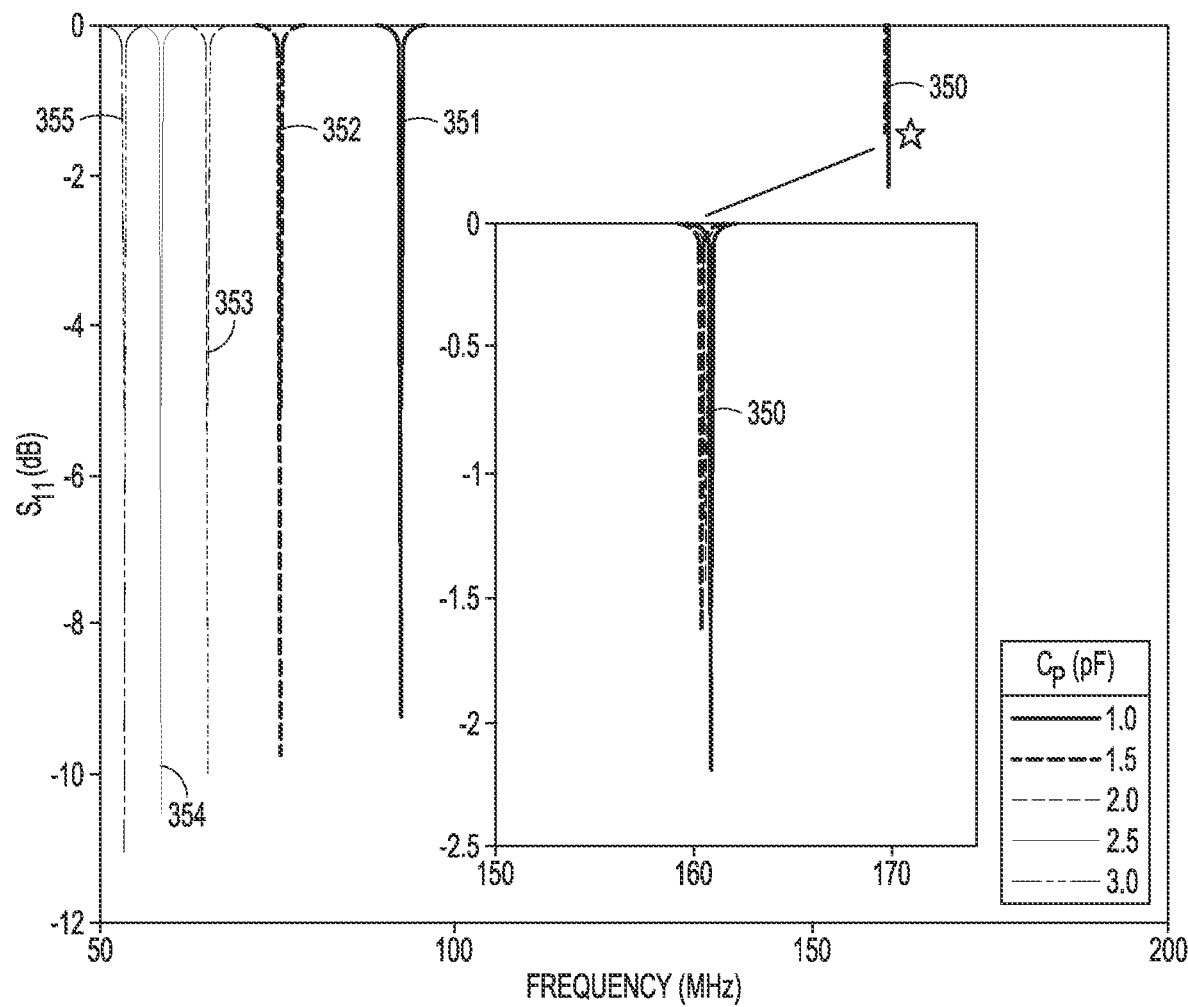
FIGS. 3A-3B show results of simulation of frequency response of an example of a coupled inductively coupled extender-inductive-capacitive system, in accordance with various embodiments.
Figure 3B:
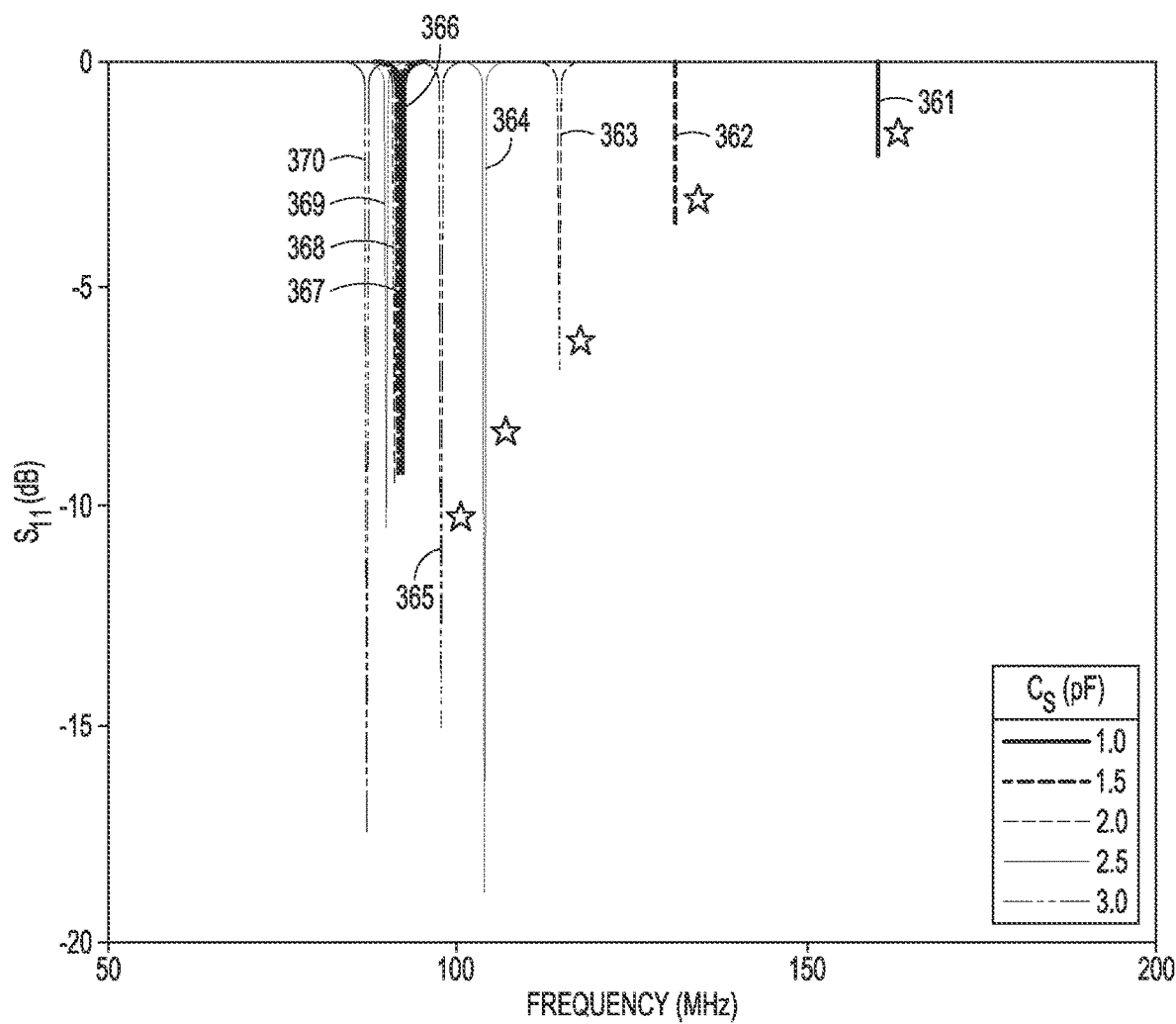

Using the circuit model of FIGS. 1C-1D, the effect of a changing soil permittivity caused by moisture content variation can be simulated. When the capacitance of the ICE ($C_p$) changes (modeled from 1 pF to 3 pF), indicative of soil permittivity at different layers of soil, the sensor resonant frequency is barely affected. FIGS. 3A-3B show results of simulation of frequency response of coupled ICE-LC system. FIG. 3A shows the effect of capacitive changes in the ICE region, not at the sensor site, on the sensor response, where FIG. 3A includes an inset for a dip 350. A dip with a star indicates a resonant frequency of the LC resonator. FIG. 3A shows several dips in the response. A dip 351 occurs for a $C_p$ value of 1.0 pF. A dip 352 occurs for a $C_p$ value of 1.5 pF. A dip 353 occurs for a $C_p$ value of 2.0 pF. A dip 354 occurs for a $C_p$ value of 2.5 pF. A dip 355 occurs for a $C_p$ value of 3.0 pF. Dip 350, with a star indicating a resonant frequency of the LC resonator, is a set of dips for the five $C_p$ values of 1.0 pF, 1.5 pF, 2.0 pf, 2.5 pF, and 3.0 pF. The sensor resonant frequency is barely affected with the set of dips, shown as dip 350, having less than 500 kHz shifts across the span of the five $C_p$ values. Similar observations were obtained when $L_{p1}$, $L_{p2}$, and $L_{p3}$ of FIGS. 1C-1D were varied.

FIG. 3B shows the effect of capacitive changes at the sensor site on the resonant sensor response. In FIG. 3B, dips with a star indicate resonant frequencies of the LC resonator. All other peaks are from the ICE portion of ICE-LC sensor system. In contrast to varying $C_p$ as shown in FIG. 3A, varying the sensor capacitance term ($C_s$), indicative of change in soil moisture at the LC sensor position, results in appreciable sensor response as shown in FIG. 3B. FIG. 3B shows several dips in the response. A dip 361, with a star indicating a resonant frequency of the LC resonator, is for the $C_s$ value of 1.0 pF. A dip 362, with a star indicating a resonant frequency of the LC resonator, is for the $C_s$ value of 1.5 pF. A dip 363, with a star indicating a resonant frequency of the LC resonator, is for the $C_s$ value of 2.0 pf. A dip 364, with a star indicating a resonant frequency of the LC resonator, is for the $C_s$ value of 2.5 pF. A dip 365, with a star indicating a resonant frequency of the LC resonator, is for the $C_s$ value of 3.0 pF. A dip 366 occurs for a $C_s$ value of 1.0 pF. A dip 367 occurs for a $C_s$ value of 1.5 pF. A dip 368 occurs for a $C_s$ value of 2.0 pF. A dip 369 occurs for a $C_s$ value of 2.5 pF. A dip 370 occurs for a $C_s$ value of 3.0 pF. The absolute magnitude of power transmission at the resonant frequency reduces when the resonant frequency of the sensor is too far away from that of ICE system. However, when both resonant frequencies are too close, the dynamic range of the sensor is reduced, where the dynamic range relates to a frequency shift upon permittivity change.

Figure 4A:
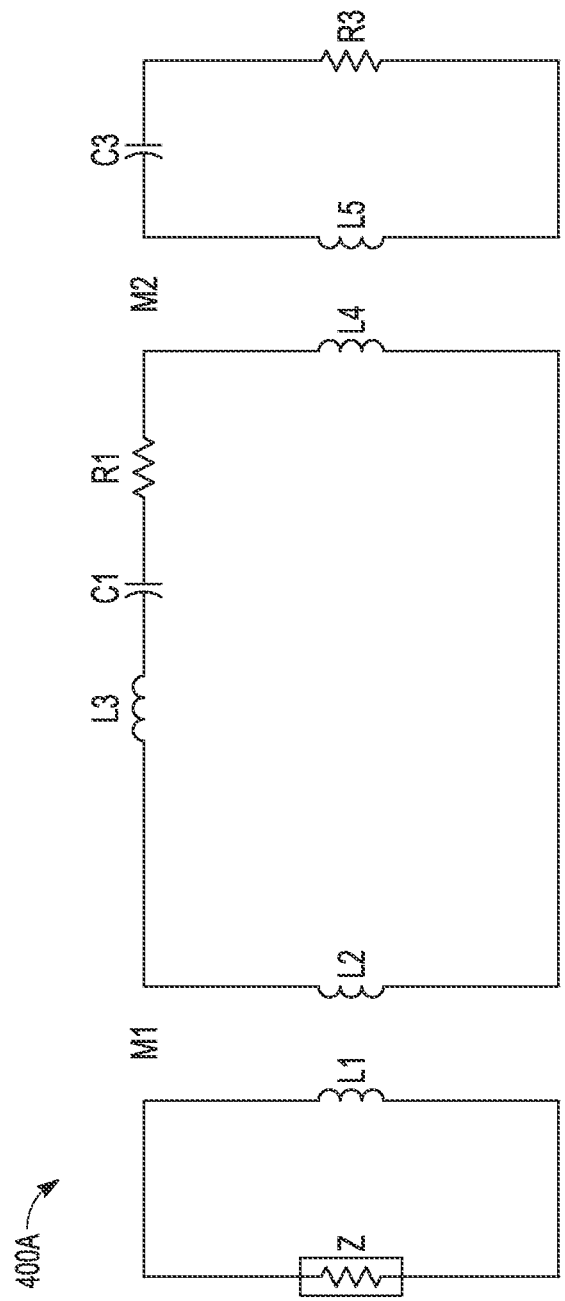
FIGS. 4A-4D illustrate the effect of additional resistive, inductive, and capacitive components in the equivalent circuit model for an example inductively coupled extender between a reader and a resonant sensor, in accordance with various embodiments.

Additional dips across the frequency range not captured by the simplified model of FIGS. 1C-1D could occur in practice. These additional dips result from harmonics and other parallel resonant frequencies within the system. The equivalent circuit model of FIG. 1D is focused only on the interested signals. In practice, additional RLC components can be present in the ICE system, which leads to additional dips throughout the frequency window. FIGS. 4A-4D illustrate the effect of additional RLC components in the equivalent circuit model for an ICE between a reader and a resonant sensor. FIG. 4A is similar to FIG. 1C with the input voltage V1 of FIG. 1C being provided by termination impedance Z. FIG. 4A shows an embodiment of an example multi-section circuit 400A having a first section, which can represent a reader, coupled to a second section, which can represent a resonant sensor, by a third section which can represent an inductively coupled extender. The first section includes impedance Z and an inductance L1. The second section includes an inductance L5, a capacitance C3, and a resistance R3. The third section includes an inductance L2, an inductance L3, a capacitance C1, a resistance R1, and an inductance L4. The mutual inductance between inductance L1 and inductance L2 has coupling coefficient k. The mutual inductance between inductance L4 and inductance L5 also has coupling coefficient k in this example.

Figure 4B:
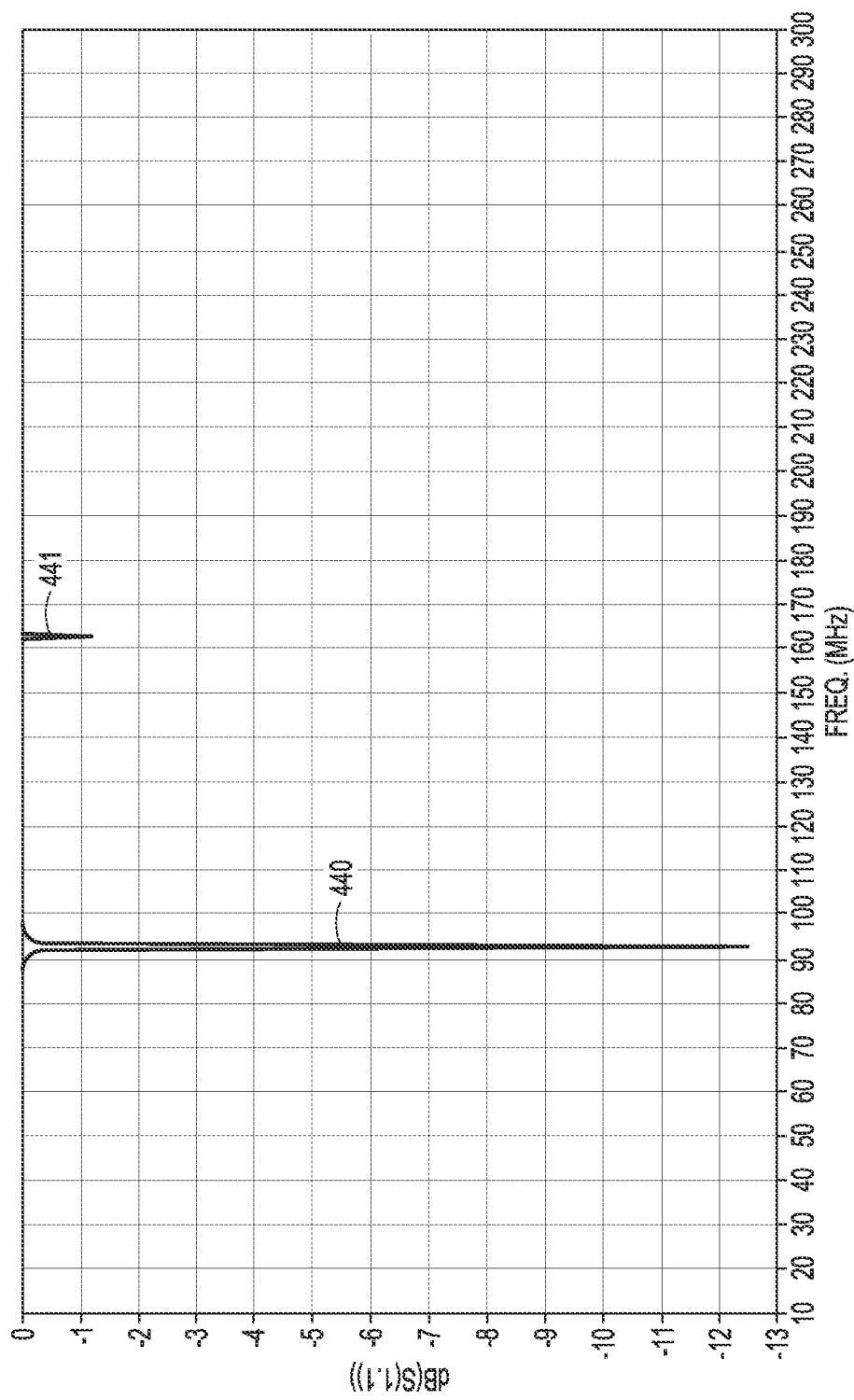

FIG. 4B is a plot of the scattering parameter $S_{11}$ versus frequency for the multi-section circuit 400A. In FIG. 4B, there are dips 440 and 441, similar to the dips shown in FIG. 2. The plot was generated for the following values of the lumped circuit elements of circuit 400A: Z=50Ω, L1=1.0 μH, k=0.3, L2=1.0 μH, L3=1.0 μH, C1=1.0 pF, R1=5Ω, L4=1.0 μH, L5=1.0 μH, C3=1.0 pF, and R3=1Ω.

Figure 4C:
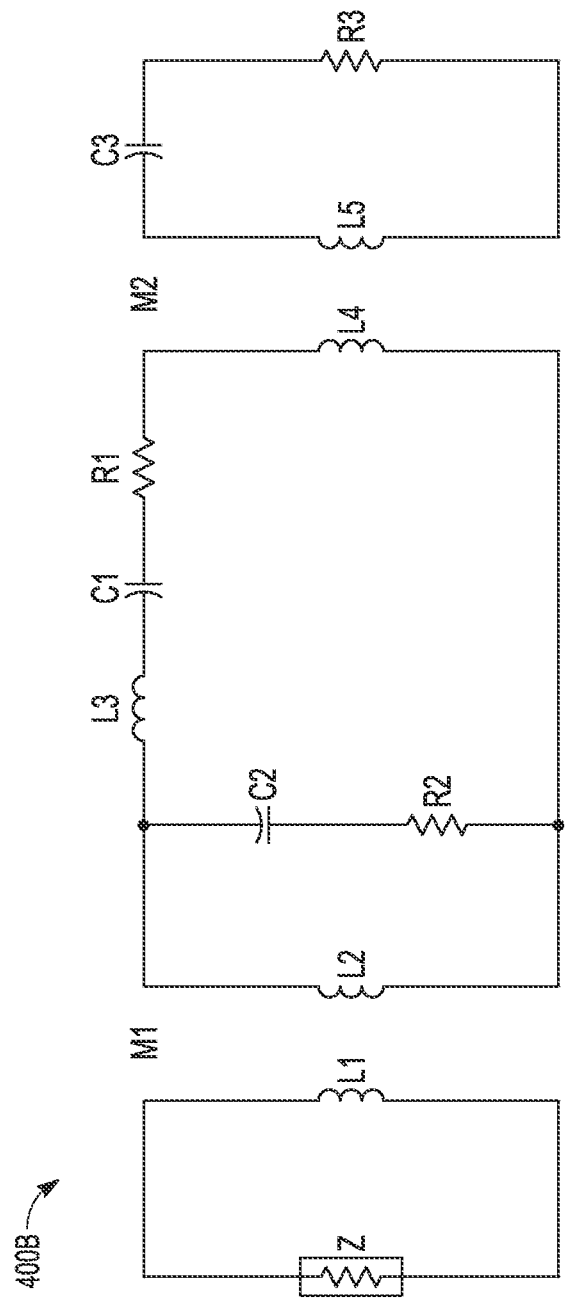

FIG. 4C shows an embodiment of an example multi-section circuit 400B that has the structure of circuit 400A of FIG. 4A with additional elements in parallel in a section of circuit 400B. Circuit 400B includes the series combination of a capacitance C2 and a resistance R2 in parallel with inductance L2 in a third section of circuit 400B corresponding to the third section of circuit 400A. In this example, the lumped circuit elements of circuit 400B have the values of the corresponding elements of circuit 400A with the additional elements of circuit 440B having the values of C2=1.0 pF and R2=10Ω.

Figure 4D:
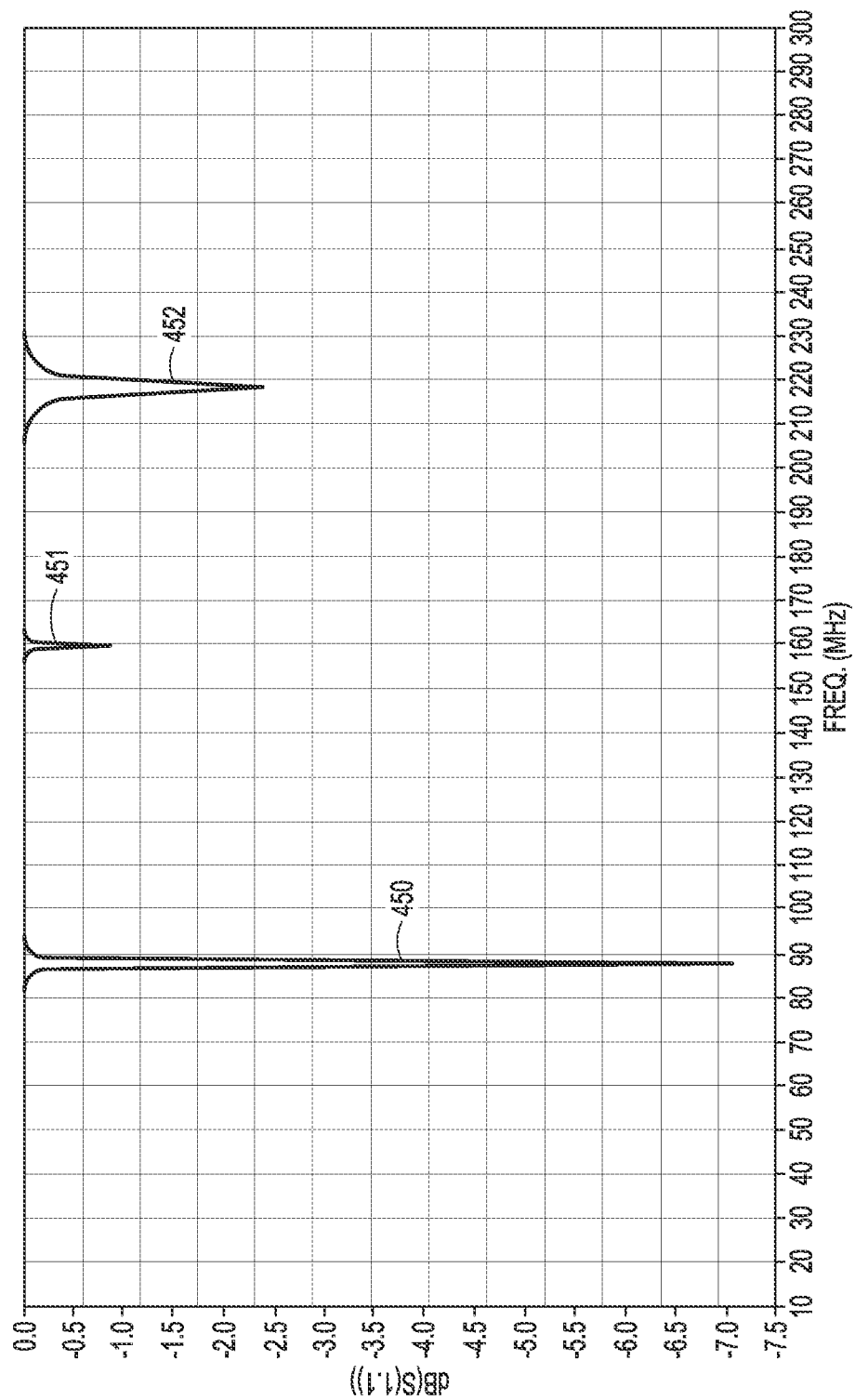

FIG. 4D is a plot of the scattering parameter $S_{11}$ versus frequency for the multi-section circuit 400B. In FIG. 4D, there are dips 540 and 541, similar to the dips shown in FIG. 4B and with additional dip 542 due to the additional components C2 and R2.

Figure 5A:
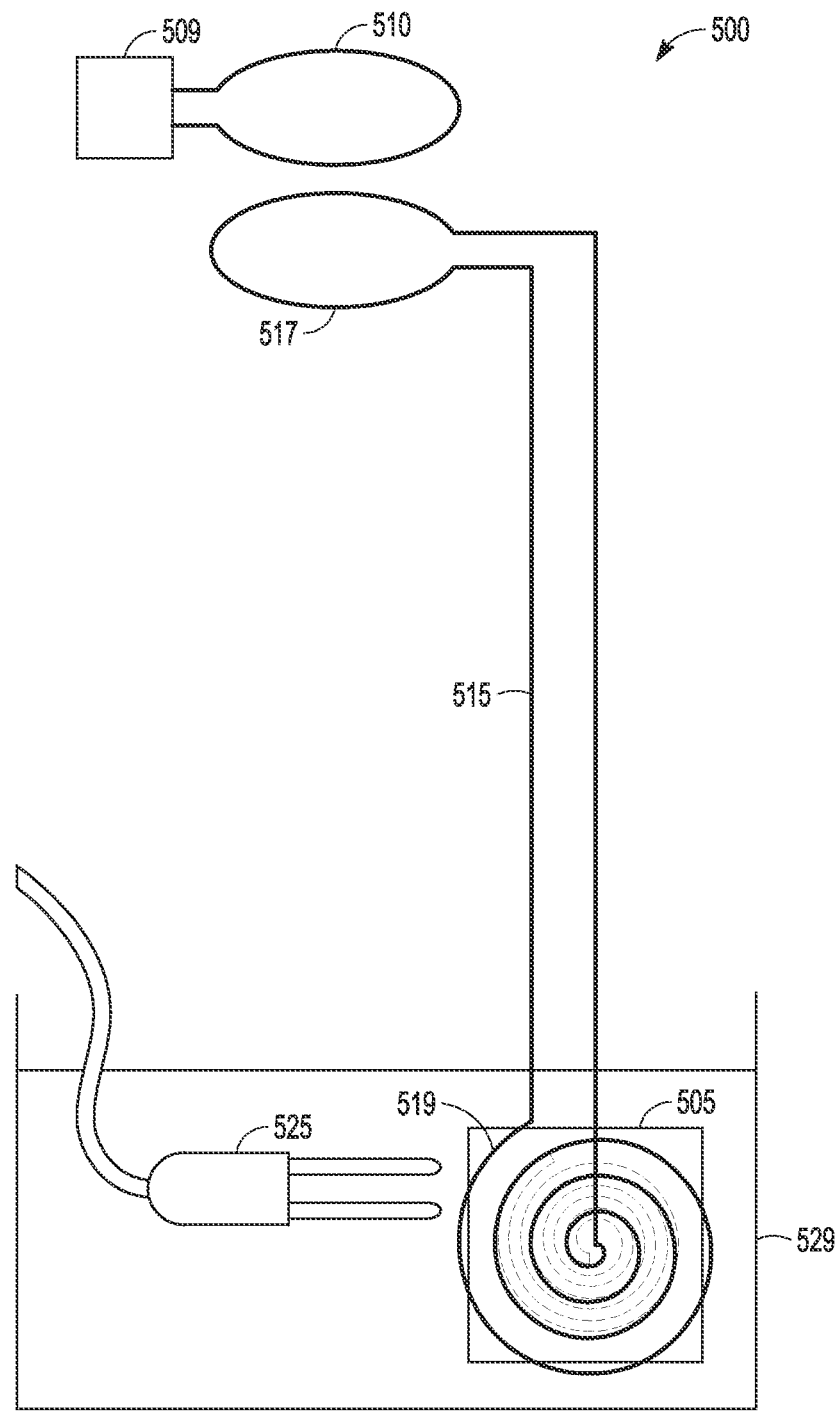
FIGS. 5A-5D illustrate prototyping of an example inductively coupled extender—inductive-capacitive sensor system and soil moisture sensing using the inductively coupled extender-inductive-capacitive sensor system, in accordance with various embodiments.

FIGS. 5A-5D illustrate prototyping an ICE-LC sensor system and soil moisture sensing using the ICE-LC sensor system in which testing of the ICE-LC sensor prototype was performed with soil samples in a laboratory. Based on the clear sensor responses from the computational models of FIGS. 1C, 1D, 4A, and 4C, a prototype sensor was fabricated for optimization and simulated field testing. FIG. 5A is a representation of an experimental setup 500 including ICE-LC sensor with wireless reader 509 and a wired capacitive soil moisture sensor 525 in a container 529 of soil. The wired capacitive soil moisture sensor 525 is used for orthogonal measurement. The experimental setup 500 includes external wireless reader 509 with a reader coil 510. The reader coil 510 is separated from an ICE 515, where the ICE 515 includes an ICE top coil 517 electrically connected to an ICE bottom coil 519, which connection can be via connection wires. The ICE bottom coil 519 is disposed proximal to a sensor resonator 505, with both the ICE bottom coil 519 and the sensor resonator 505 disposed in the container 529 of soil. This experimental setup 500 was built on a wooden dowel using the following geometries for a potential read range of up to 1 meter deep in the soil of the container 529. The dimensions for the prototype ICE-LC sensor system included the reader coil 510, the ICE top coil 517, and the ICE bottom coil 519 having an outer diameter of 40 mm, a pitch of 4 mm, and a wire gauge of 18. The dimensions included the resonant sensor 505 having an outer diameter of 40 mm, a pitch of 2.5 mm, and a trace width of 2 mm.

The resonant sensor coil 505 was fabricated using an etching method. In brief, a spiral trace of the coil was designed in Inkscape™ and plotted with a sharpie on a Pyralux® sheet using a Silhouette cutting/plotting machine. Upon drying, the Pyralux® sheet was transferred to an etching solution consisting of 2:1 of hydrogen peroxide (3 wt %) and hydrochloric acid (37%). Acetone was used to remove the sharpie mask.

In fabrication of the prototype ICE-LC system, molds with different designs of spiral traces were designed in Solidworks® and three-dimensional (3D) printed using Ultimaker® 3. Twenty-gauge copper wires were then fit into the slots of the printed molds. Wires in between the ICE top coil 517 and the ICE bottom coil 519 were taped onto wooden dowel, which serves as support. The wooden dowel was 3 ft in length with a 0.5 inch diameter. The ends of the wires were soldered to form a complete closed circuit.

Similarly, in the fabrication of reader coil 505, copper wire was fit into a 3D printed mold. The ends of the wire were soldered to BNC-wire leads, to connect to a VNA. A commercial VNA was used for s-parameter measurements using the designed software of the commercial VNA.

To mitigate noise, the wires connecting the two coils 517 and 519 of the ICE system 515 were shielded and all tests utilized the same resonant sensor 505 affixed to the ICE bottom coil 519 of the ICE system 515. The system was tested with and without the resonant sensor 505, which confirmed the interrogation between the external reader 509 and the sensor of the sensor resonator 505. The sensor resonator 505 was interrogated via the ICE-LC system at frequency dips around 140 MHz, when in proximity to ICE bottom coil 519.

Figure 5B:
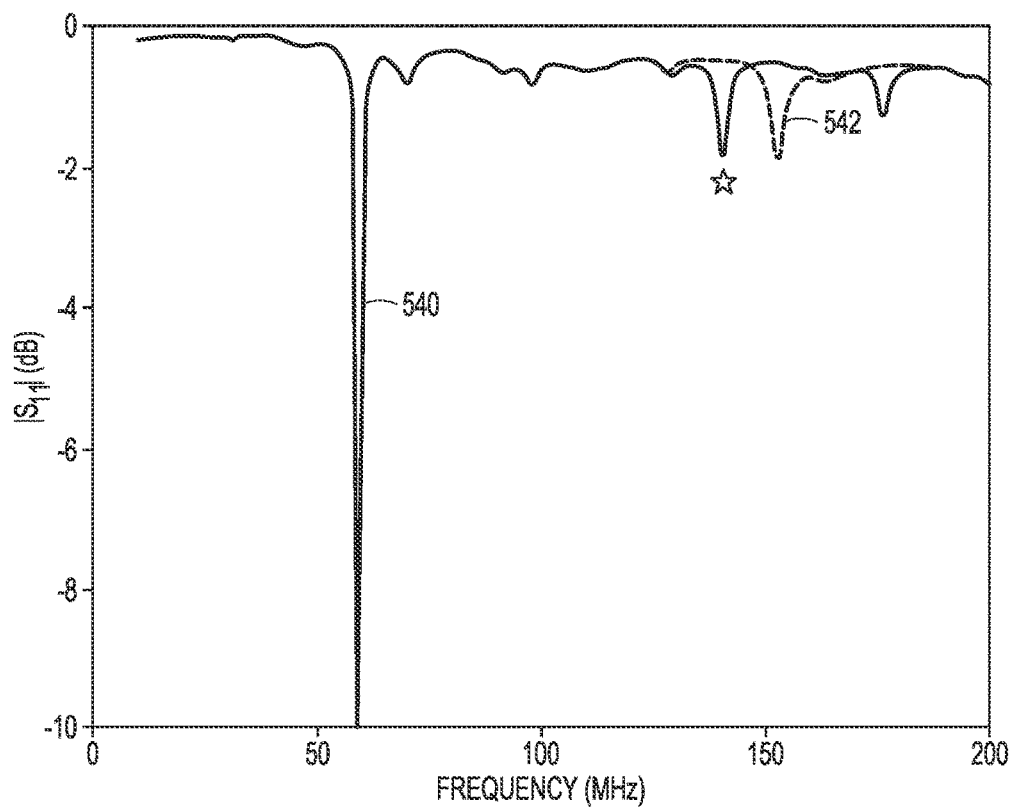

FIG. 5B illustrates effect of soil on the resonant frequency of the resonant sensor with sensor via curve 540 and without sensor via curve 542. These dips are dependent on the parallel LC components present within the system including that of the sensor resonator 505 and ICE 515. Different alignments of the reader coil 510 on the ICE top coil 517 also showed negligible effect on the resonant frequency of the resonator 505 sensor due to the constant parasitic capacitance between the ICE bottom coil 519 and the resonant sensor coil 505, demonstrating the system's capability to overcome positional limitations.

Figure 5C:
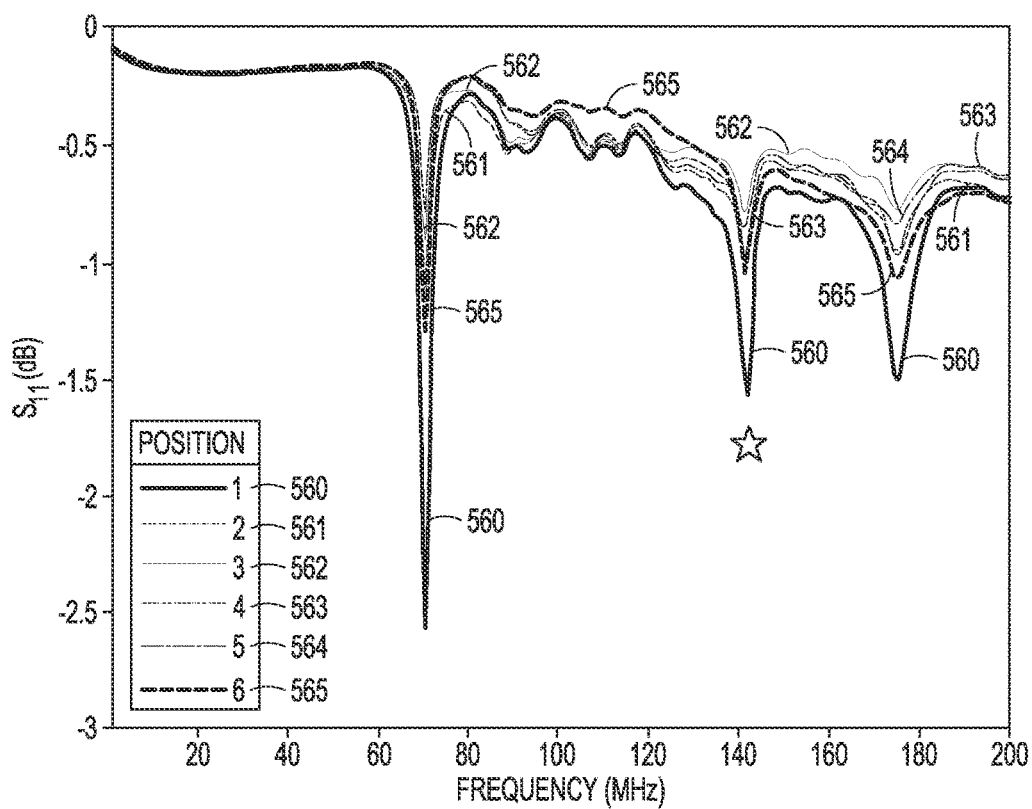

FIG. 5C is a plot of the scattering parameter $S_{11}$ versus frequency for raw data of the sensing system of FIG. 5A when the relative position between the reader coil 510 and the ICE top coil 517 is varied. FIG. 5C represents the sensor signal in response to varying position between the reader coil 510 and the ICE top coil 517. Sensor signals are shown for the position of the reader coil 510 being moved and oriented relative to the ICE top coil 517 in six different positions. Signal curves 560, 561, 562, 563, 564, and 565 result from positions 1, 2, 3, 4, 5, and 6 of the six different positions. When looking at the minimum resulting from the resonant sensor 505, the resonant frequency, represented by the star, is 141.47±0.093 MHz with a 95% confidence. Although the dip resulting from the ICE system also shows robustness towards positional variation, the sensitivity towards the environment was low as shown in FIG. 5D.

Figure 5D:
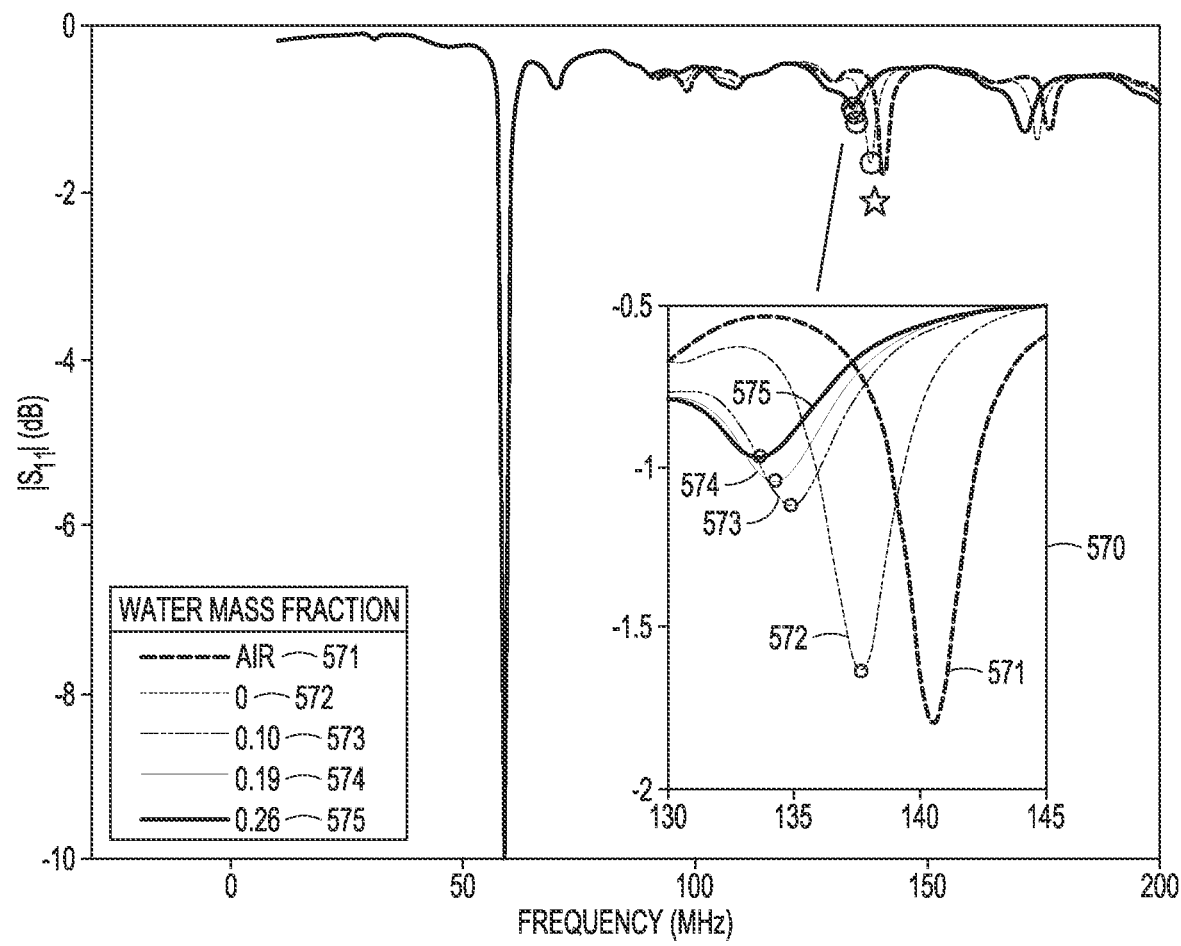

FIG. 5D illustrates effect of increasing soil moisture content on the resonant frequency and amplitude of the resonant sensor response for the experimental setup 500 of FIG. 5A. The resonant sensor 505 was tested in soil with varying moisture content levels. FIG. 5D is a plot of the scattering parameter $S_{11}$ versus frequency for different water mass fractions. A star indicates a resonant frequency of the sensor resonator 505. An inset 570 shows signal curves 571, 572, 573, 574, and 575 near the resonant frequency. Signal curve 571 is for air as a control. Signal curve 572 is for zero water mass fraction. Signal curve 573 is for 0.10 water mass fraction. Signal curve 574 is for 0.19 water mass fraction. Signal curve 575 is for 0.26 water mass fraction. The resonant frequency and the dip magnitude both decrease as soil moisture increases. This is consistent with higher relative permittivity of soil as more water is present, increasing the capacitance and therefore reducing the resonant frequency, as described in Equation 3. A higher moisture level also increases the conductance of the soil creating a more lossy environment and therefore decreasing the dip magnitude with less power absorbed by the LC sensor 505.

Figure 6A:
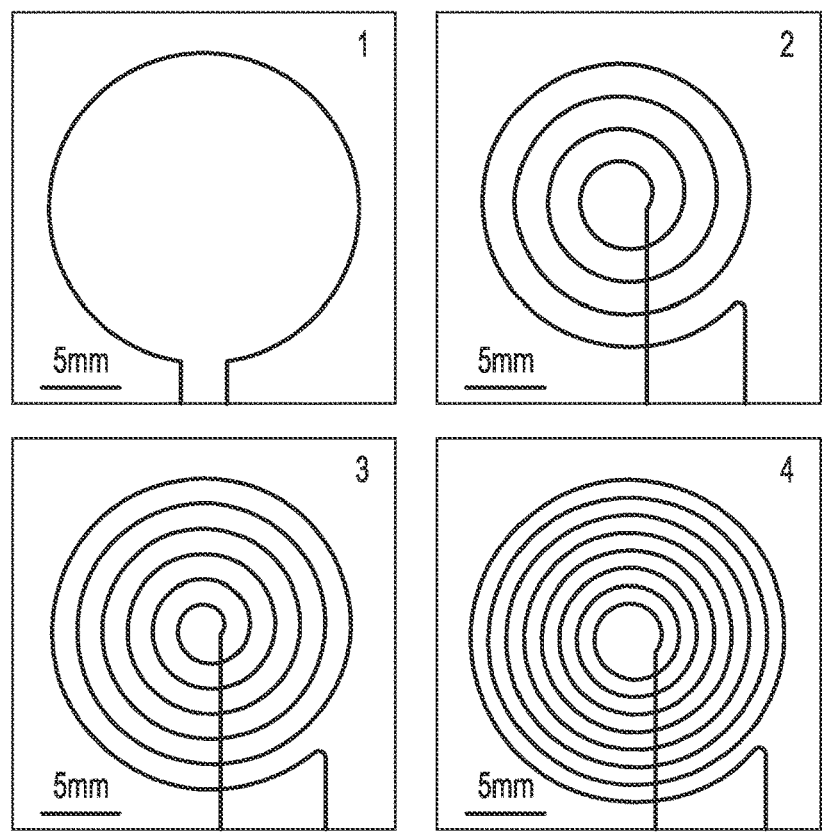
FIG. 6A shows different geometries of coils used for sensitivity experiments for sensitivity analysis of different parts of an inductively coupled extender system, in accordance with various embodiments.

To further optimize the sensor response, effects of the sizes of reader coil, ICE top coil, and ICE bottom coil on sensor sensitivity to different soil moisture levels was investigated. Four different geometries were used, while keeping the outer diameters constant at 4 cm. FIG. 6A shows different geometries of coils used for sensitivity experiments for sensitivity analysis of different parts of the ICE system. The four different geometries are shown as geometry 1 with one turn, geometry 2 with four turns having a 4 mm pitch, geometry 3 with six turns having a 3 mm pitch, and geometry 4 with eight turns having a 2 mm pitch. When investigating each of the coils using the above geometries, the other coils were fixed at four turns.

High clay content soil was dried overnight at 120° C. and crushed to smaller than 1 cm clumps. The dried soil was then measured at 350 g and added with 0, 40, 80, and 120 mL of water. The soil was then homogenized using a spatula to minimize the heterogeneity of soil, resulting in water mass fraction of 0, 0.10, 0.19, and 0.26 or soil moisture content of 0.8, 5.9, 9.6, and 12.5% (measured using capacitive sensor), respectively. The ICE bottom coil and the sensor were buried in the soil and the soil was swapped with the different moisture levels. The extracted resonant frequencies were normalized by subtracting with the minimum resonant frequency (at highest soil moisture content).

Figure 6B:
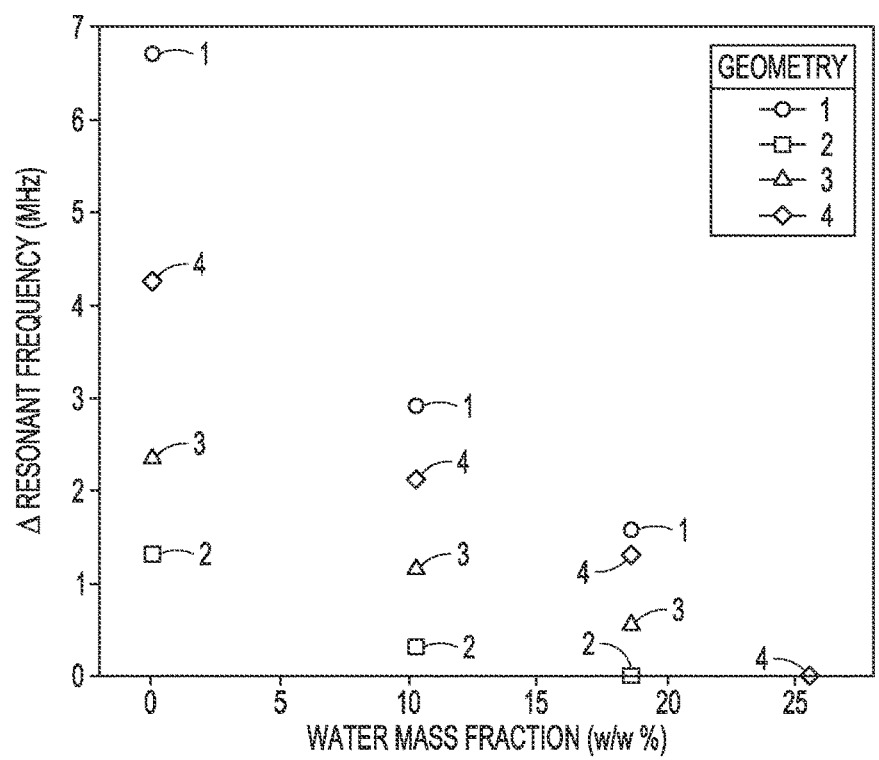
FIG. 6B shows delta resonant frequency versus water mass fraction for the geometries of FIG. 6A, in accordance with various embodiments.

These circuit geometries affect the inductances and $C_p$ values of the ICE-LC sensor system. Varying the sizes of the reader coil and the ICE top coil does not affect sensor response outside of having different starting resonant frequencies of the sensor. However, different geometries for an ICE bottom coil yield different sensitivity, with the greatest sensitivity obtained from the single loop. FIG. 6B shows Δ (delta) resonant frequency versus water mass fraction for the four geometries 1, 2, 3, and 4. The Δ resonant frequency is defined by the subtraction of actual resonant frequency to the minimum actual resonant frequency throughout the span of water mass fraction.

Figure 7A:
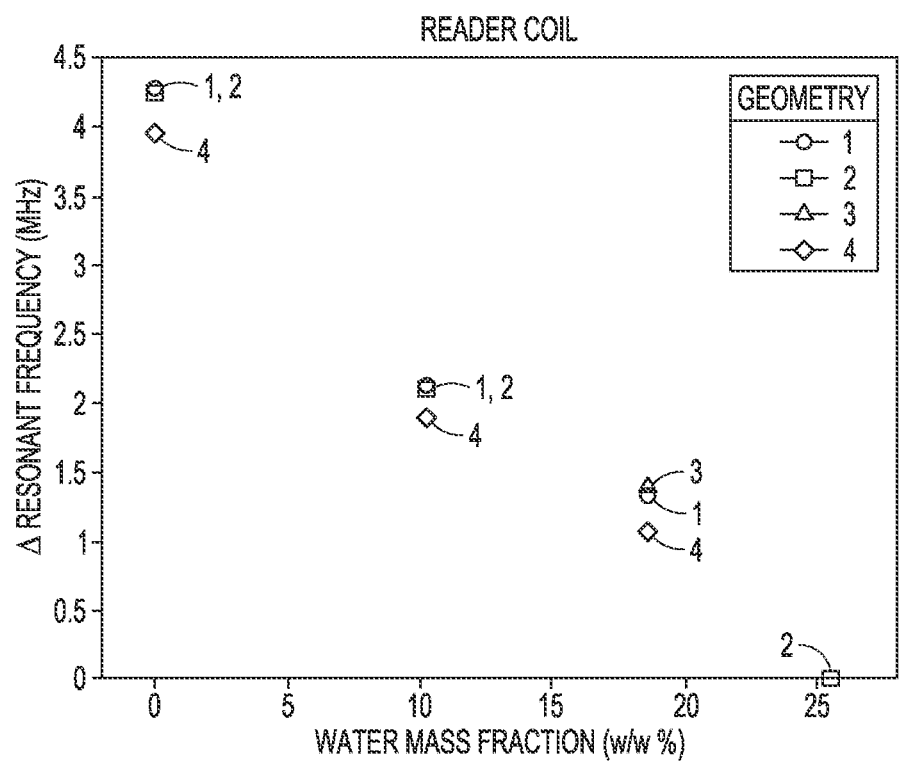
FIGS. 7A-7C illustrate effect of geometries of a reader coil, an inductively coupled extender top coil, and an inductively coupled extender bottom coil on the sensitivity of a sensor signal, in accordance with various embodiments.
Figure 7B:
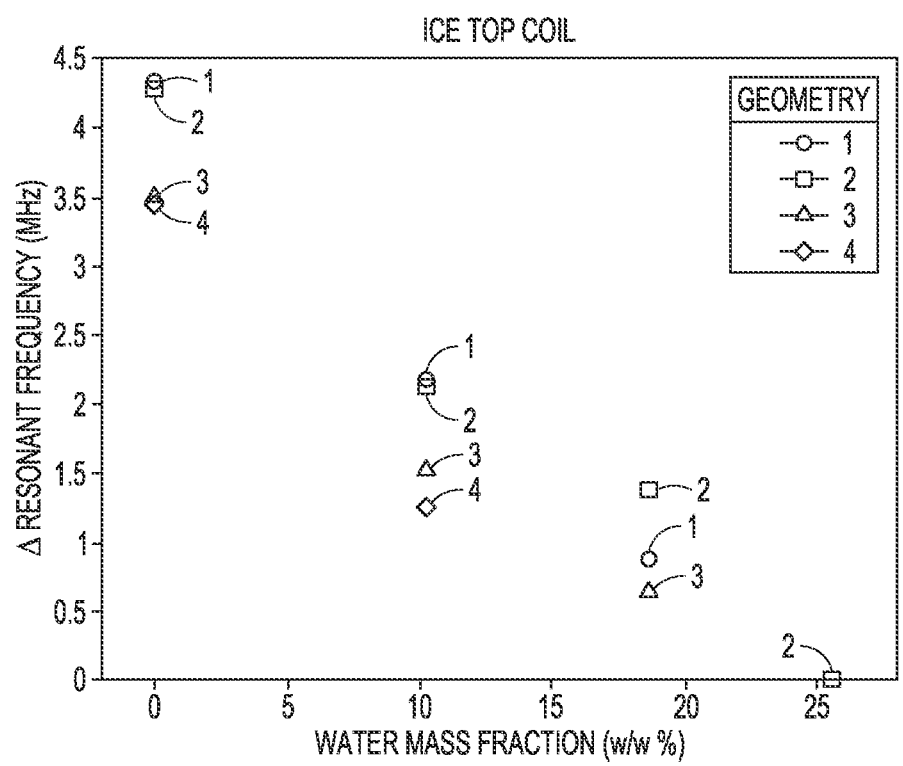
Figure 7C:
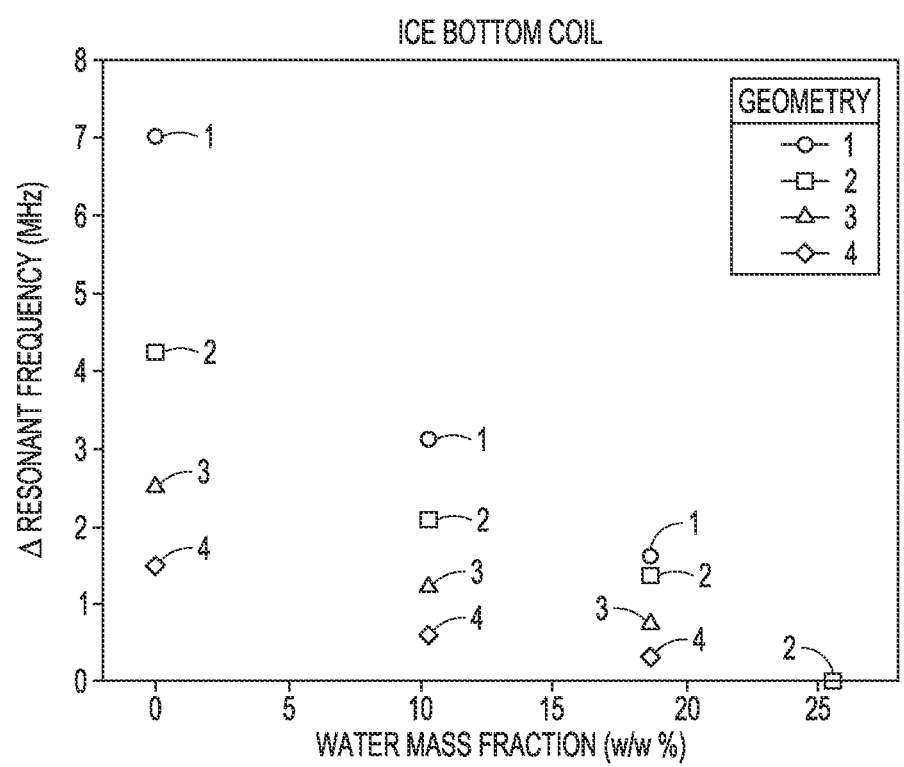

To examine the sensitivity dependence on the readout coil and ICE system, the reader, ICE top, and ICE bottom coils were each varied with the four geometries 1, 2, 3, and 4 and tested in soil environment consisting of various moisture content. FIGS. 7A-7C illustrate effect of geometries of the reader coil, ICE top coil, and ICE bottom coil on the sensitivity of the sensor signal. FIG. 7A shows data points for Δ resonant frequency versus water mass fraction for a reader coil having geometries 1, 2, 3, and 4. FIG. 7B shows data points for Δ resonant frequency versus water mass fraction for an ICE top coil having geometries 1, 2, 3, and 4. FIG. 7C shows data points for Δ resonant frequency versus water mass fraction for an ICE bottom coil having geometries 1, 2, 3, and 4. The sensitivity was not strongly influenced by the geometry of the reader coil and the ICE top coil. However, the sensitivity is greatest with the one turn geometry of the ICE bottom coil. This can be due to the lesser parasitic capacitance in between the sensor and the ICE bottom coil, thus having more electric field fringing into the soil environment.

Figure 8A:
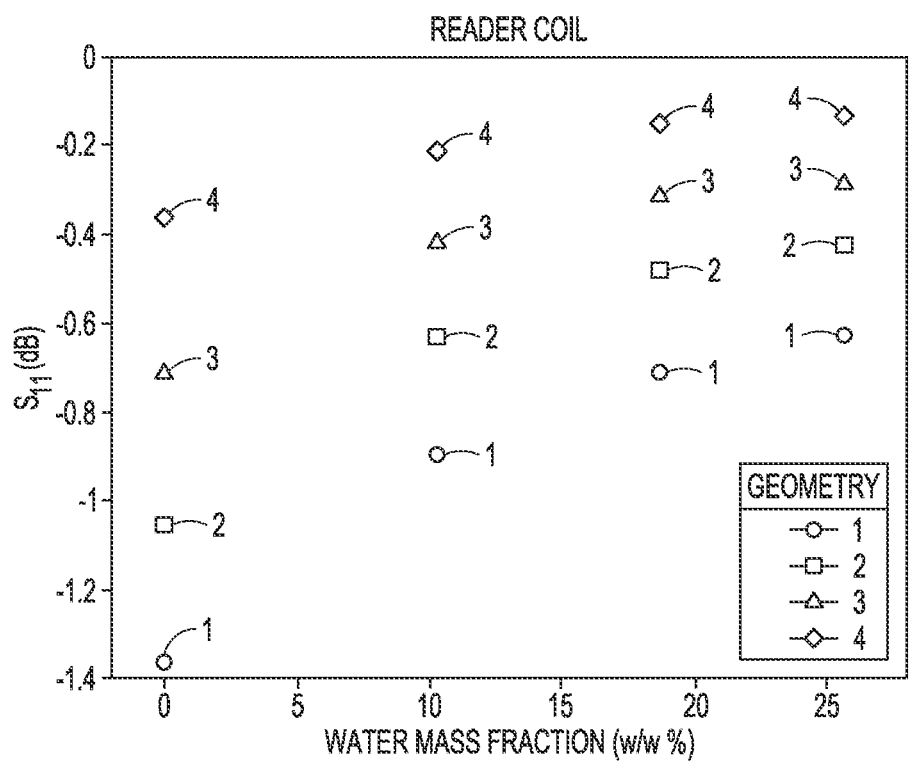
FIGS. 8A-8C shows the effect of geometries of a reader coil, an inductively coupled extender top coil, and an inductively coupled extender bottom coil on the dip magnitude at the resonant frequency of a sensor, in accordance with various embodiments.
Figure 8B:
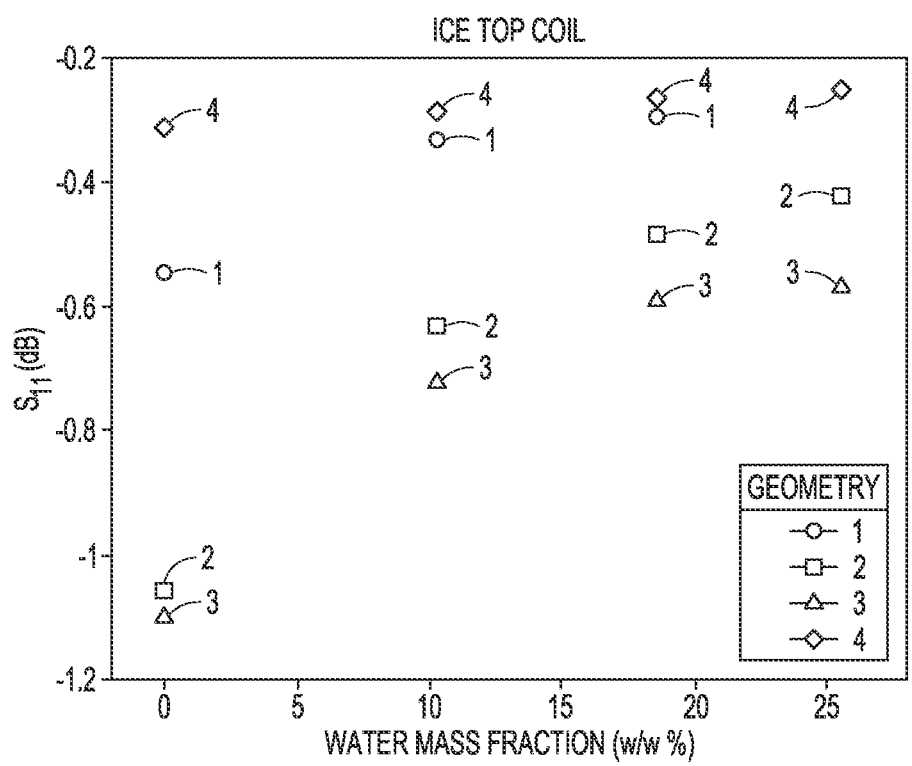
Figure 8C:
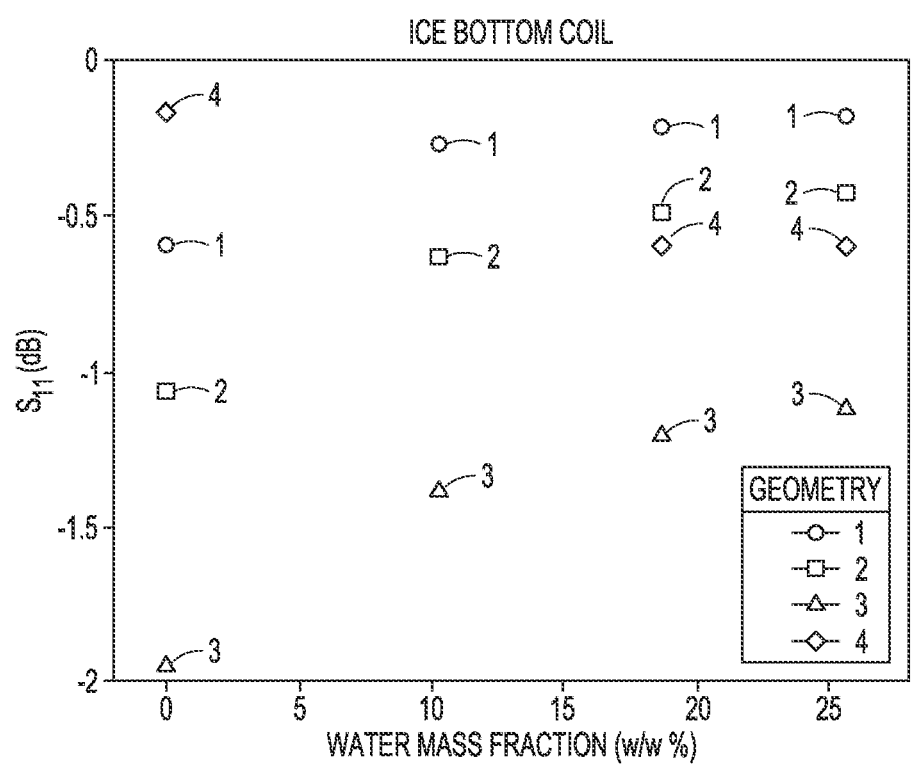

In terms of power transfer, the $|S_{11}|$ value at the resonant frequency of sensor is used for evaluation. Changing the geometry of the reader coil resulted in most power transferred when it is at one turn, followed by four turns, six turns, and eight turns. In considering power transfer based on the geometry of the readout, the ICE top, and the ICE bottom coils, the dip magnitudes of the resonant frequencies in FIGS. 8A-8C were extracted to evaluate the power transfer. These magnitudes are subtracted by a control, which involves the readout and ICE system (in air) but without the sensor. The sensor received the most power when reader coil consists of a single loop, whereas the ICE top and bottom coils consists of 6 turns, 3 mm pitch, which is the closest length to the sensor coil. FIGS. 8A-8C shows the effect of geometries 1, 2, 3, and 4 of the reader coil, the ICE top coil, and the ICE bottom coil, respectively, on the dip magnitude at the resonant frequency of the sensor. Further experiments showed a slightly higher power transferred when the reader coil and the ICE top coil consists of a loop, whereas the ICE bottom coil consists of 4 turns (data not shown).

On the other hand, tuning each ICE top and bottom coil both resulted in the highest power transferred with six turns, followed by four, one, and eight turns. However, tuning the ICE top coil while having the reader and the ICE bottom coils fixed at one and 4 four turns, respectively, showed highest power transferred when the ICE top coil is one turn. This indicates the matching of inductance between the interrogating coils can be significant for a higher power transfer. Therefore, the reader coil and the ICE top coil can be set at one turn each and the ICE bottom coil can be set at four turns to provide a sufficient $|S_{11}|$ value. As indicated in FIG. 6B, using one turn for the ICE bottom coil results in highest sensitivity and the four turn geometry ensures the sensor signal is detectable in high moisture environments. The single turn ICE bottom coil did not provide detectable signal in high moisture environment with this geometry combination (data not shown).

The ICE-LC sensor system evaluated for optimization in the studies related to FIGS. 5A-8C was then tested with simulated field conditions of soil dehydration and rehydration events to establish metrics of sensor response with respect to linearity, limits of detection, robustness. The ICE-LC sensor system was placed in a beaker of low clay soil hydrated to approximately 35% moisture content. The beaker was then continuously monitored using the ICE-LC sensor until the moisture content dried to between 20% and 25%. This was repeated three times to determine the sensor stability and reproducibility of the sensor response to soil moisture content. Initially high clay soil was used for this experiment, but it was difficult to simulate field conditions at one meter depth with a smaller beaker as the high clay content soil was prone to cracking upon dehydration. In addition, rehydrating the soil resulted in mini-reservoirs, which skewed the resonance frequency response.

Figure 9A:
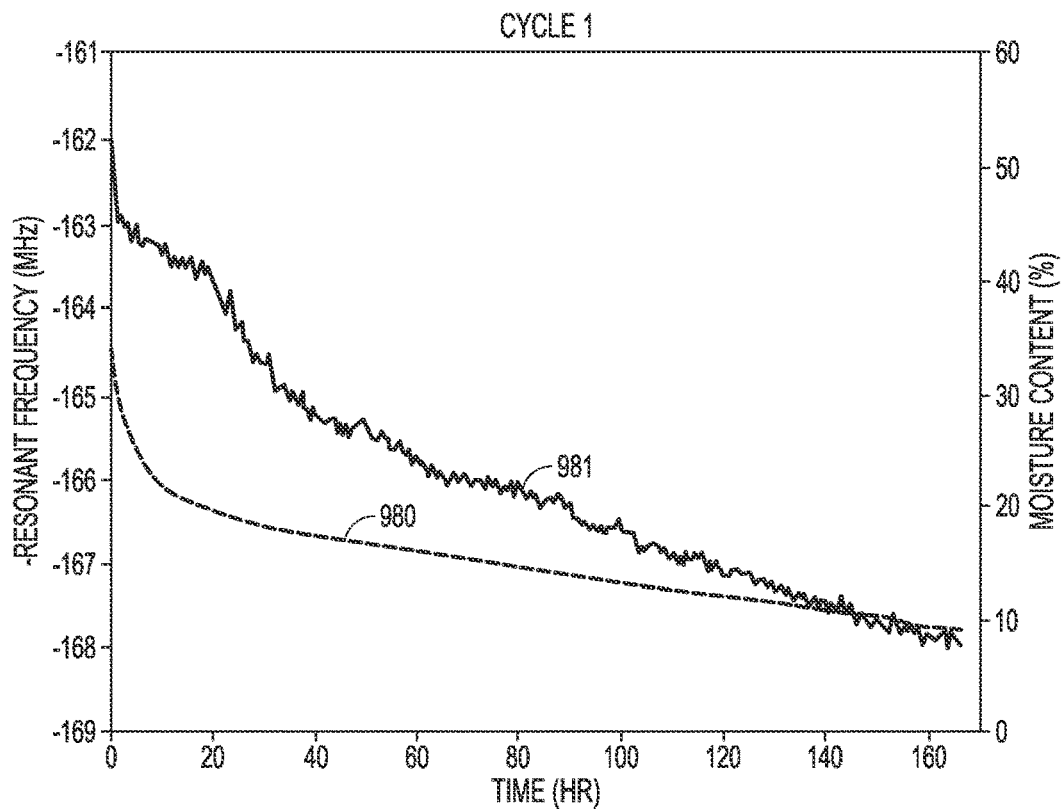
FIGS. 9A-9C illustrate measurements of the evaporation process in a high clay content soil using an inductively coupled extender—inductive-capacitive sensor system along with a Vernier soil moisture sensor, in accordance with various embodiments.
Figure 9B:
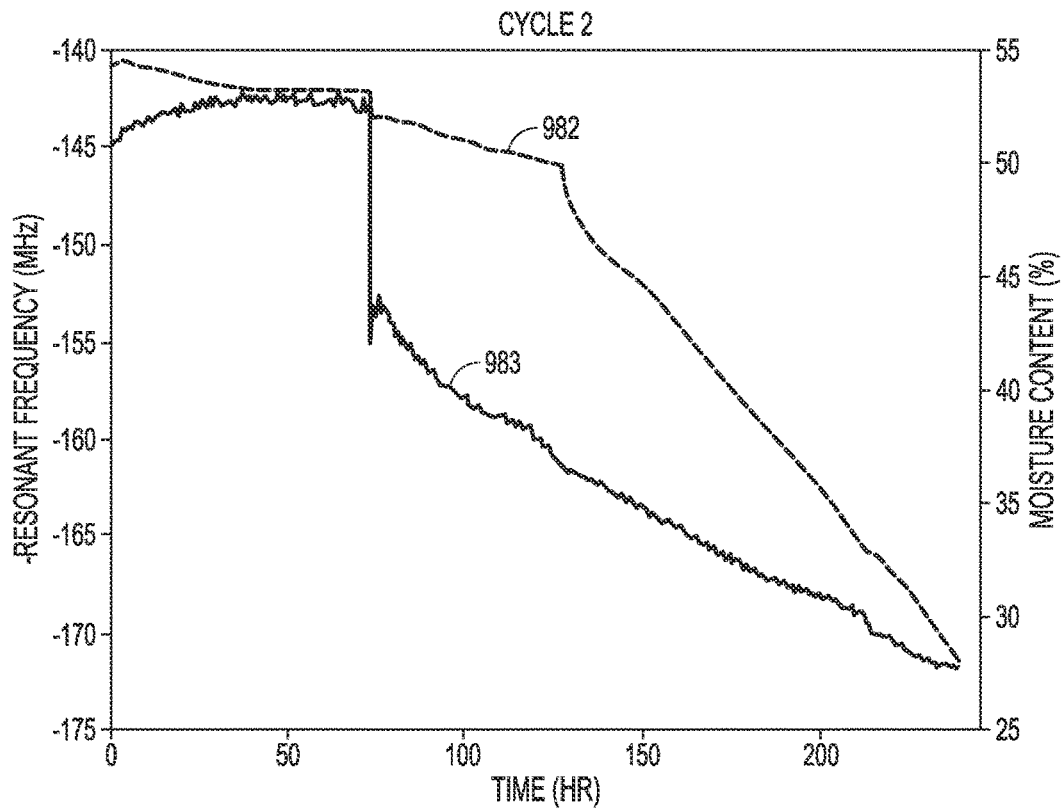
Figure 9C:
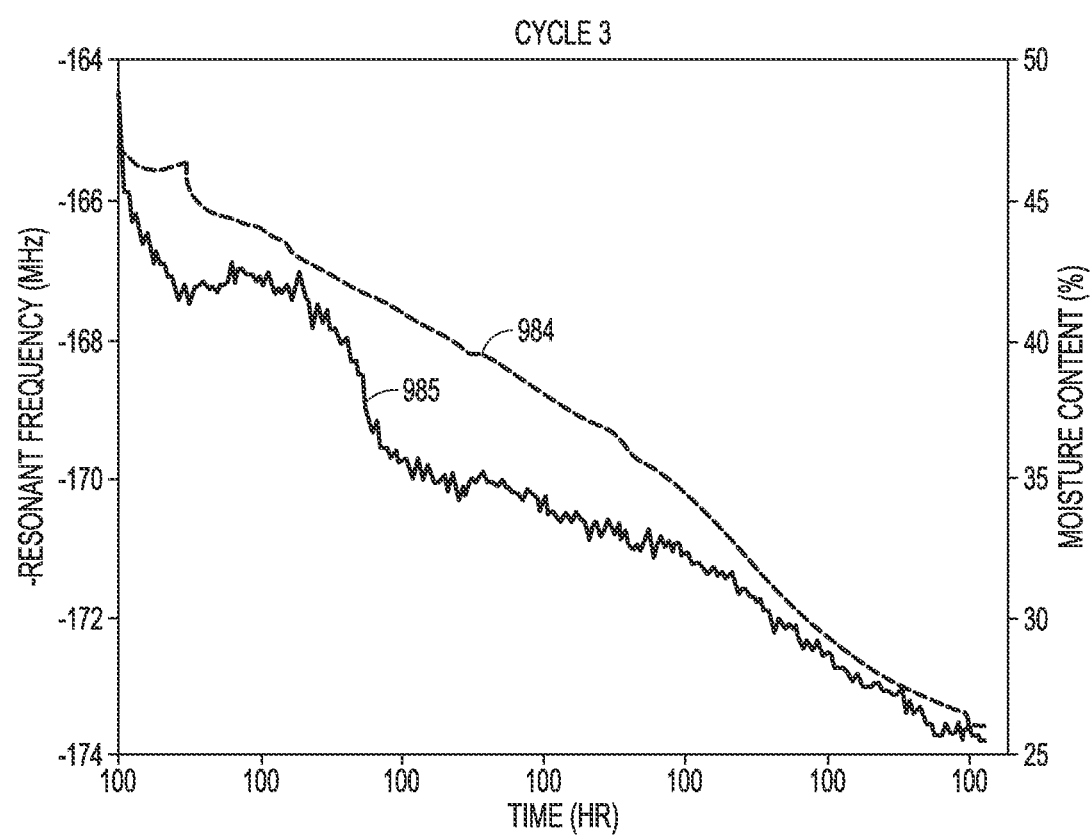

FIGS. 9A-9C illustrate measurements of the evaporation process in a high clay content soil using an ICE-LC sensor system along with a Vernier soil moisture sensor. FIG. 9A plots curve 980 as moisture content versus time and curve 981 as resonant frequency versus time for a first cycle. FIG. 9B plots curve 982 as moisture content versus time and curve 983 as resonant frequency versus time for a second cycle. FIG. 9C plots curve 984 as moisture content versus time and curve 985 as resonant frequency versus time for a third cycle. Inconsistencies of the sensor system occurred with high clay content soil. High clay content soil was observed to form clumps and cracks throughout an evaporation process in the soil. Both the starting frequencies and the gain of the sensor response were inconsistent when compared to the moisture content measured by Vernier sensor. In the second cycle, excess water was used initially to wet the soil. The sudden jump in resonant frequency was observed after the excess free running water was removed. This 'cracking' phenomenon could be a limitation to use, as the sensor relies on a homogenous soil body with smooth changes in permittivity caused by water addition, not stochastic jumps caused by cracking and flooding with water.

Figure 10A:
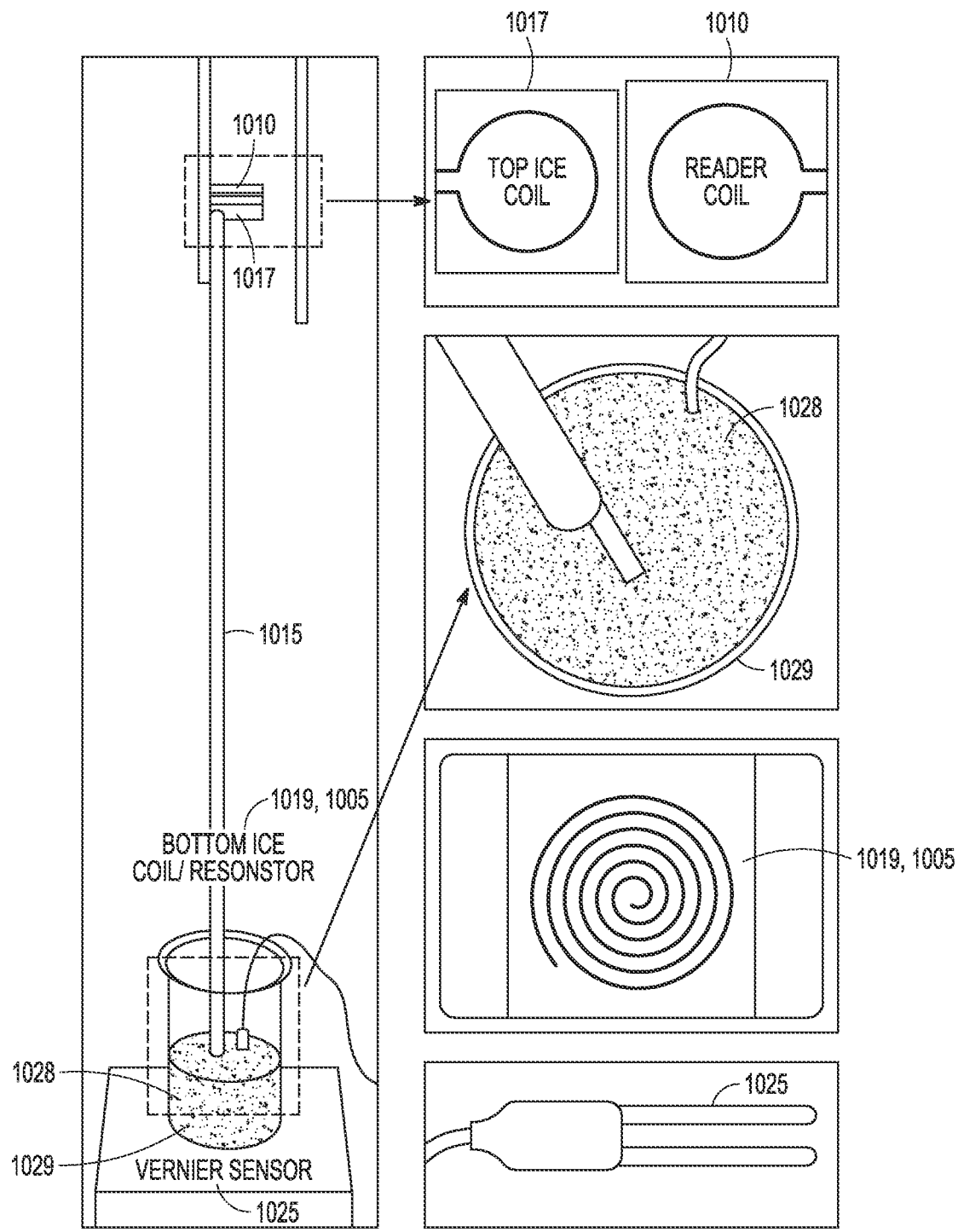
FIGS. 10A-10C show an experimental setup of an inductively coupled extender—inductive-capacitive sensor system and simulation of field conditions with the experimental setup, in accordance with various embodiments.
Figure 10B:
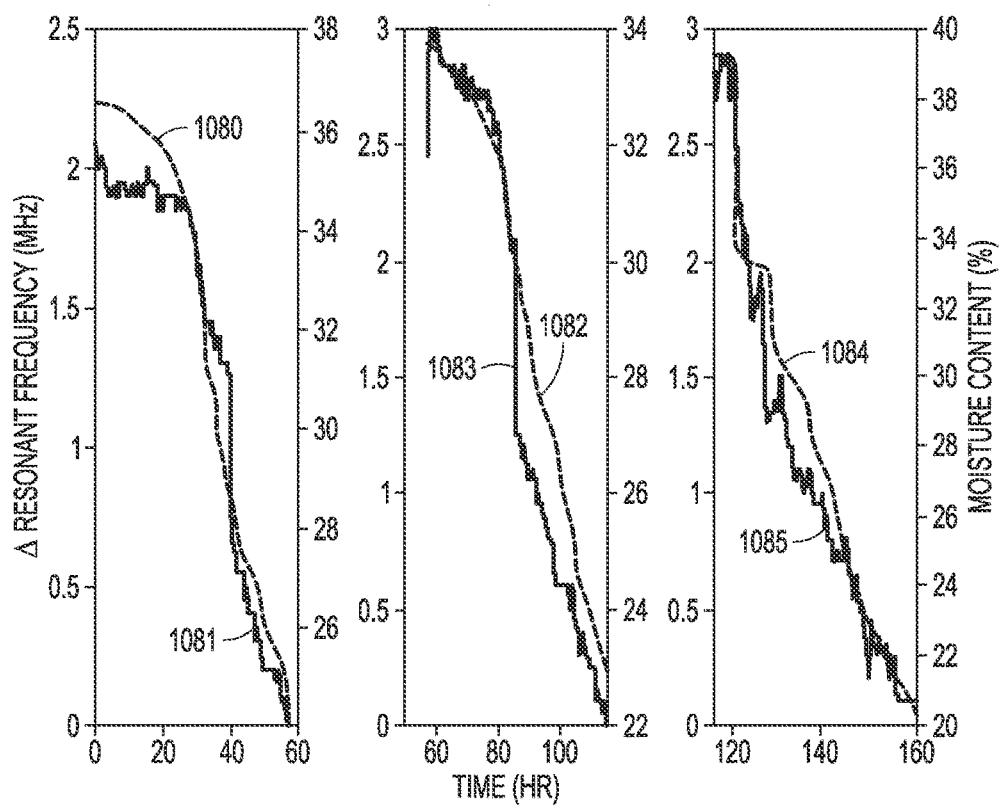
Figure 10C:
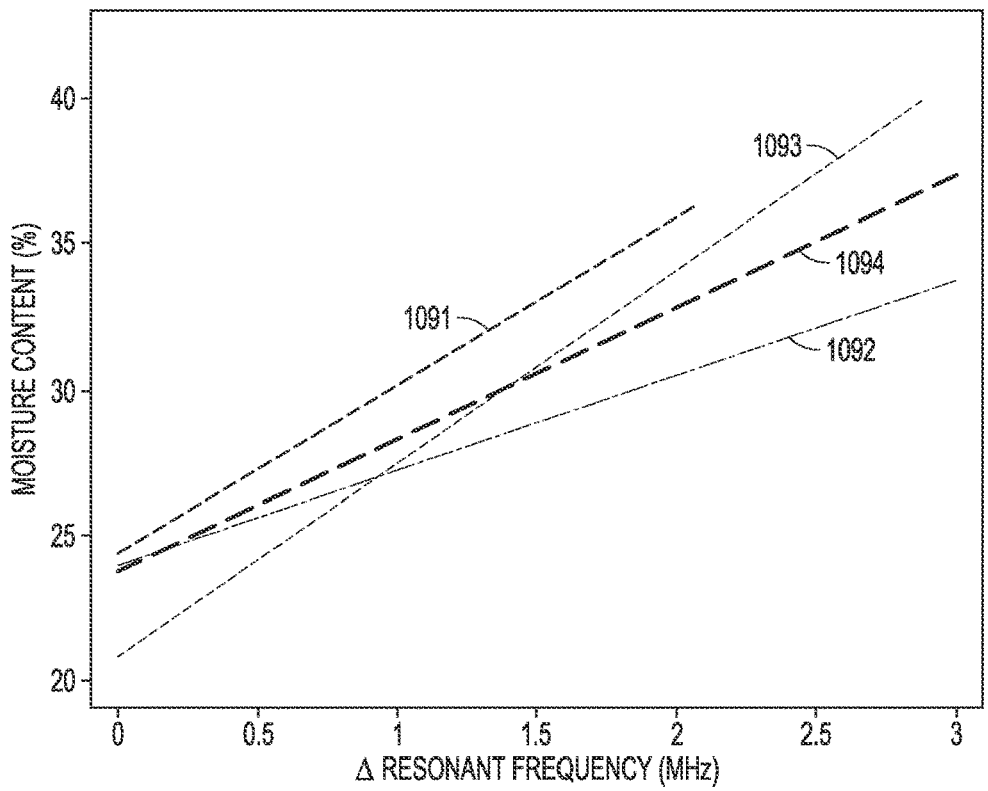

FIGS. 10A-10C show an experimental setup of an ICE-LC sensor system and simulation of field conditions with the experimental setup. FIG. 10A illustrates the experimental setup of the ICE-LC sensor system with external reader and a capacitive moisture sensor for orthogonal measurement. The left side of FIG. 10A shows the vertical extent of the ICE-LC sensor system from the sample location at which a vernier sensor 1025, a resonant sensor 1005, and a bottom ICE coil 1019 are arranged in a soil sample 1028 in a container 1029. The bottom ICE coil 1019 of ICE 1015 is electrically connected to a top ICE coil 1017. The top ICE coil 1017 is arranged with but separate from reader coil 1010. The right side of FIG. 10A shows a closer view of components of the experimental setup of FIG. 10A: vernier sensor 1025 providing a soil moisture sensor, a top view of the bottom ICE coil 1019 oriented above the resonant sensor 1005, sample soil 1028 in container 1029, and the top ICE coil 1017 with the reader coil 1010.

FIG. 10B are plots of A resonant frequency versus time and moisture content versus time for three time periods. Data 1080 in the first period, measurement data 1082 in the second period, and measurement data 1084 in the third period are for moisture content. Measurement data 1081 in the first period, measurement data 1083 in the second period, and measurement data 1085 in the third period are for Δ resonant frequency. FIG. 10B shows an effect of resonant frequency as a result of decreasing soil moisture content with three dehydration periods. After the first two dehydration periods, the container of soil was rehydrated. In general, the frequency response for the ICE-LC system is correlated with a capacitive-based soil moisture sensor moisture content response in FIG. 10B. The base frequency did change after each rehydration experiment, which is likely caused by soil structure changes, uneven water infiltration, and the difference in sensing regions of the capacitive and ICE-LC sensors. The data was normalized to the highest resonant frequency during the rehydration event.

FIG. 10C shows parity plots and gain of the three-period soil dehydration experiments. The three periods correspond to three measurement runs. The sensor gains, defined as change in resonant frequency relative to change in moisture, were a gain of 5.76 for the first run was 5.76, a gain of 3.32 for the second run, and a gain of 6.65 for the third run. Overall, for the three periods, the gain was 4.52. The sensor gains were similar for the first and third runs, but an exceptionally lower gain in the second run was observed. This was caused by the discontinuity observed between 30-35% moisture content that could be due to water accumulation around the LC sensor. Without this outlier region, the gain for the second run becomes 5.58, which is closer to the other cycles. For the first run, a linear fit 1091 was made. For the second run, a linear fit 1092 was made. For the third run, a linear fit 1093 was made. For the overall runs, a linear fit 1094 was made. The linear fit on all the independent dehydration cycles resulted in an $R^2$ of 0.745. A correlation coefficient, R, indicates how strong of a linear relationship there is between two variables. The square of R, $R^2$, is the coefficient of determination, with values $0 \leq R^2 \leq 1$, and is used to analyze how differences in one variable can be explained by a difference in a second variable. Evaluating the residuals, the mean absolute error and the root mean squared error when correlating resonant frequency to soil moisture content measured by the capacitive sensor were 2.05% and 2.41%, respectively. Sources of error between methods could be electronic noise from both methods and variations in macro soil structure causing non-uniform rehydration throughout the soil (i.e., dryer on the surface where the capacitive sensor is located vs. lower where the resonant sensor is placed). Ways to reduce variation in gain include standardizing fabrication of an ICE-LC sensor, using polymer sleeves to protect the shielding from getting wet, and using a low loss (low relative permittivity) core material instead of a wooden dowel for the post of the sensor.

Figure 11A:
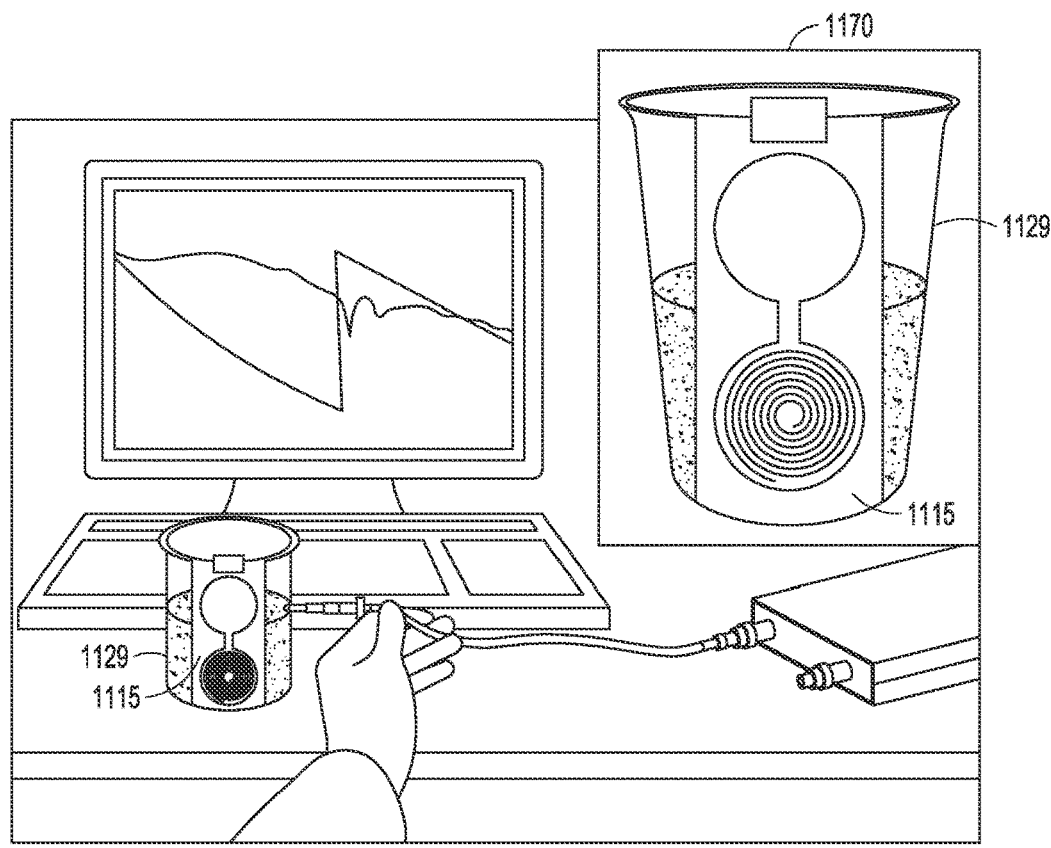
FIGS. 11A-11B illustrate an experimental arrangement of a planar, compact form factor for an inductively coupled extender—inductive-capacitive sensor system and results of application of the experimental arrangement, in accordance with various embodiments.
Figure 11B:
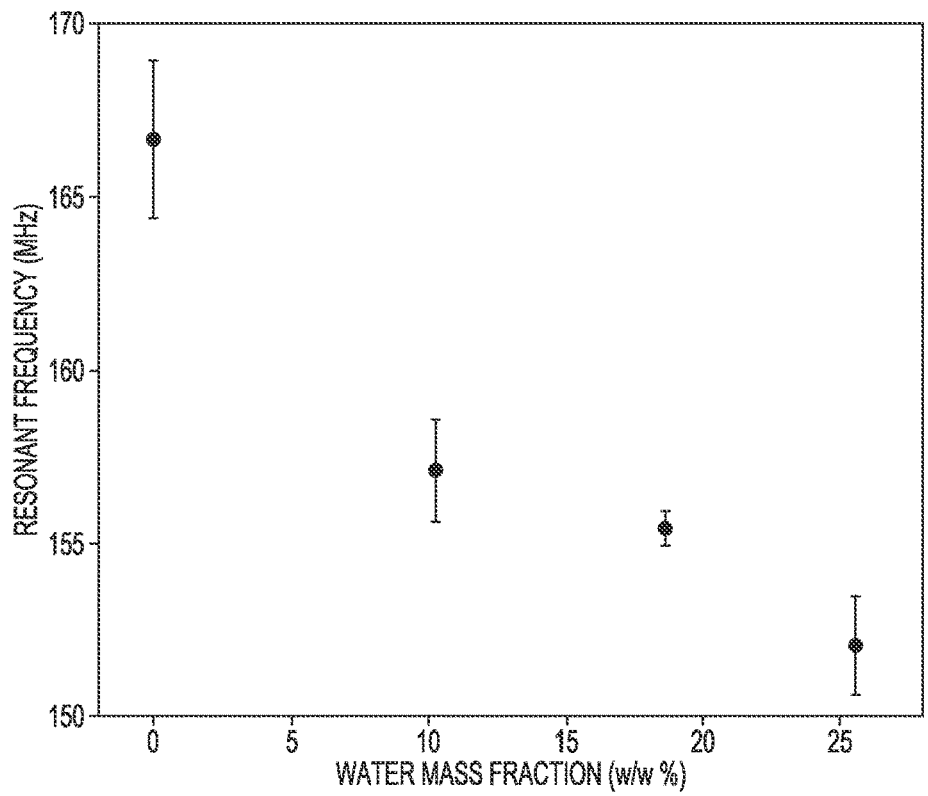

FIGS. 11A-11B illustrate an experimental arrangement of a planar, compact form factor for an ICE-LC sensor system and results of application of this experimental arrangement. The ICE-LC sensor was designed in planar form to demonstrate the ability to adapt the ICE scheme to different applications in soil moisture measurement and beyond. FIG. 11A shows the experimental setup of planar compact system testing soil moisture content through a glass beaker 1129. The planar version 1115 of the ICE-LC sensor was designed in Rhinoceros® software and fabricated on a single sheet of copper-clad polyimide (DuPont Pyralux®) by printing onto the Pyralux® and etching. The planar ICE-sensor was attached, by taping, onto an external surface of the glass beaker 1129 (a 600 mL beaker), which represents a free-standing pot or planar rhizotron. Soil moisture content was monitored through the container 1129. The beaker 1129 was filled with soil of different water mass fractions, i.e., different moisture content, with each level being repeated more three times to simulate a real-world scenario, where an operator would periodically assess each sensor with a hand-held reader. In this experiment, the reader was removed and replaced between trials (not static setup). In this manner, the reader coil was positioned manually and inconsistently each time when taking measurement, to validate the system robustness.

FIG. 11B shows data points of resonant frequency as a function of water mass fraction of soil in the beaker 1129, providing a frequency response of increasing soil moisture content. The number of data points in this figure is four with three being the number of repeated measurements. The average standard deviations of 1.41 MHz between the three replicates (error bars) demonstrate the positional independence of the reader. A major source of this deviation is likely due to the soil structural variation between the replicates. Nonetheless, this shows that in other use scenarios, where an extended read range (>5 cm) is not needed, the ICE in a compact, planar form can be used to provide positional independence between the reader coil and LC sensor. This can have an immediate impact in other LC sensor applications, such as temperature, pressure, humidity, chemicals, gases, etc., that suffer from positional variance.

Conventionally, low-cost, passive LC sensors were best suited to static applications that allowed for proximal placement of the reader. Embodiments for ICE-LC sensor systems, as taught herein, can dramatically extend possible applications of LC sensors by overcoming step-off distance limitations and positional limitations. An ICE-LC sensor was designed and simulated using an equivalent lumped element model in Matlab® and in Advanced Design System, which showed the potential for extending read range and providing positional independence. The initial prototype was further optimized to increase the sensitivity of the resonant sensor, determining that a single loop top coil and four loop bottom coil for an ICE structure provides the best suitability for the experiments conducted, with respect to a set of coils for an ICE structure, in terms of sensitivity and signal strength for the LC resonant sensor. This best design from the testing was further tested using simulated field conditions to determine the feasibility of the sensor to monitor soil moisture conditions over a growing season. The sensor showed strong correlation ($R^2$ of 0.745, MAE of 2.05%) between the ICE-LC sensor frequency response and the measured soil moisture content. The linear gain (4.52% water content/MHz) was observed in the range of 20% to 35% moisture content. The ICE-LC system was also demonstrated in a planar, compact form factor to demonstrate utility in applications that require positional independence but not extended read range. Improved sensor performance, with respect to decreased parity error to established techniques and more repeatable gain, by focusing on manufacturing methods and materials for the sensor. These sensors can be deployed to field locations to provide better spatiotemporal data for modeling and precision agriculture efforts.

Ability to monitor soil moisture content via resonant frequency of ICE-LC sensor was performed using low clay soil (play sand) samples in a laboratory. A container of 600 mL of dry soil had 150 mL of water, which was allowed to infiltrate freely into the soil. Soil used in the experiment was air dried in oven at 60° C. overnight. The ICE-LC sensor's bottom coil and resonant sensor was buried in the soil along with a capacitive soil moisture sensor (Vernier) approximately two inches below the surface of the soil. The external reader, connected to a VNA, was placed in proximity to the top coil of the ICE-LC sensor and automatic scans were taken every 30 minutes. At each time point, the soil moisture content was also recorded according to the capacitive sensor in the soil. Soil was allowed to dehydrate until the soil moisture content was approximately 20-25%, whereupon an additional 100 mL was used to rehydrate the soil. This rehydration step was repeated two times. The extracted resonant frequencies between different cycles were normalized by subtracting the maximum resonant frequency of the corresponding dehydration cycle and then adding a negative sign to match the moisture content trend measured by the capacitive sensor.

Figure 12A:
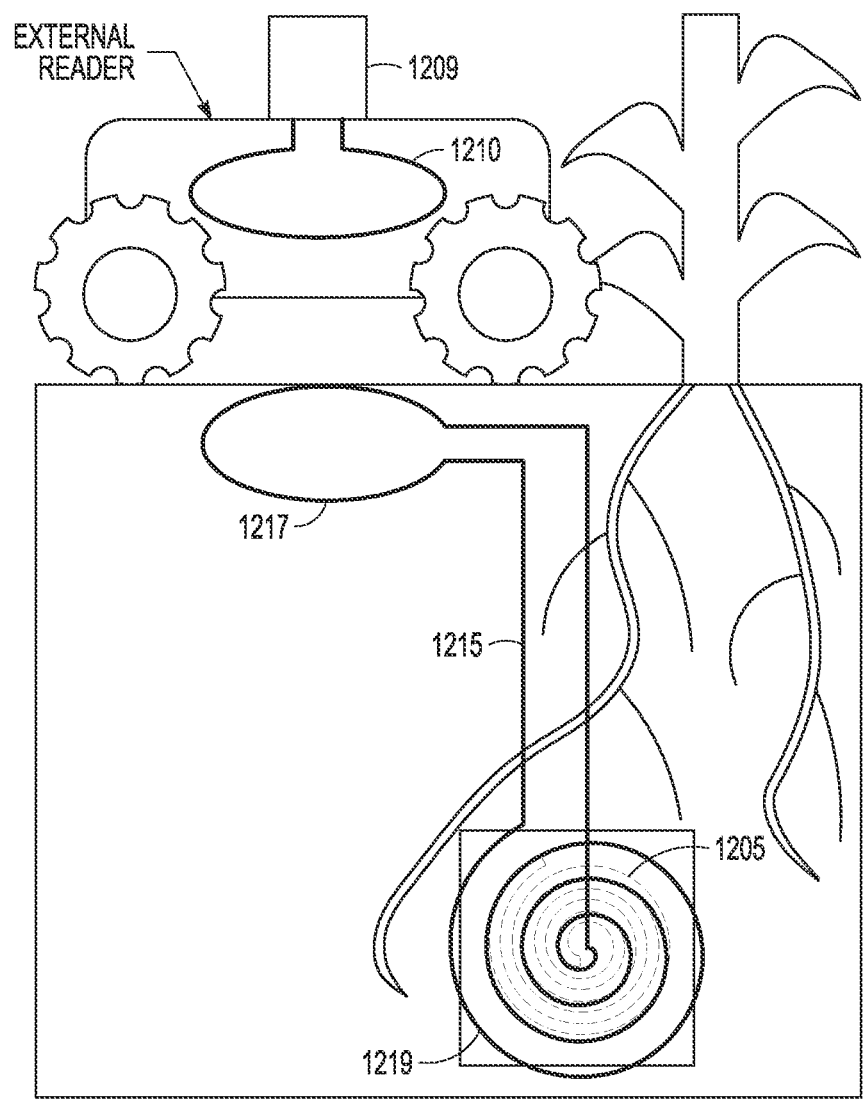
FIG. 12A illustrates an application of an inductively coupled extender—inductive-capacitive moisture sensor in an agricultural setting, in accordance with various embodiments.
Figure 12B:
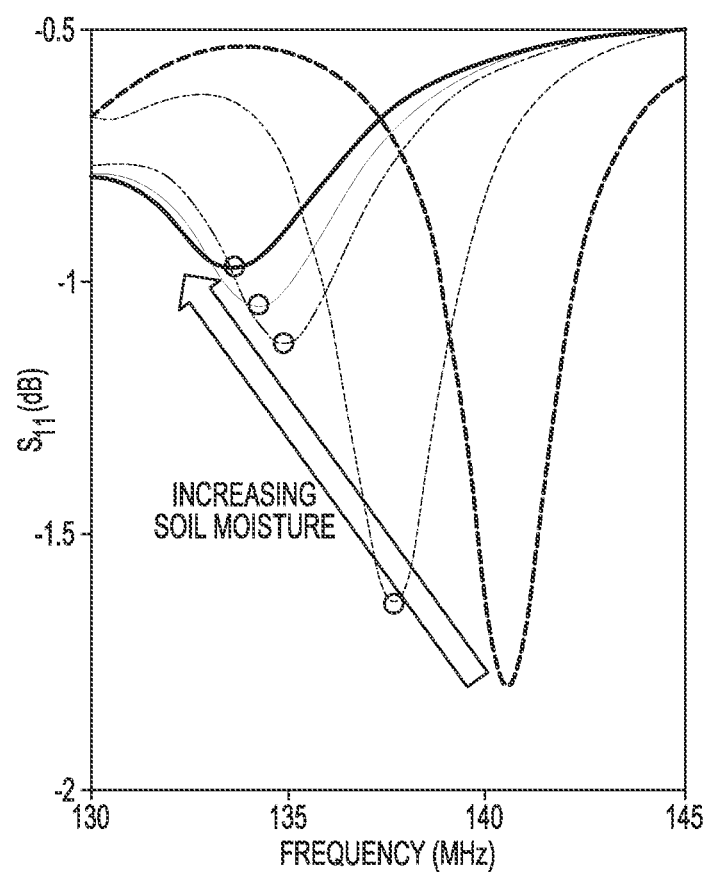
FIG. 12B is a plot of the absolute value of a $S_{11}$ scattering parameter versus frequency that indicates decreasing of resonant frequency with increasing soil moisture, in accordance with various embodiments.

FIG. 12A illustrates an application of an ICE-LC moisture sensor 1215 in an agricultural setting. The ICE-LC moisture sensor 1215 includes a bottom ICE coil 1219 arranged with respect to a resonant sensor 1205 located a distance below the surface. The ICE-LC moisture sensor 1215 includes a top ICE coil 1217 vertically connected to the bottom ICE coil 1219 via electrical wires. Depending on the application, top ICE coil 1217 can be horizontally connected, or have some other separating orientation, to the bottom ICE coil 1219 via electrical wires. The electrical wires can be housed in a support structure. An external reader 1209 includes a reader coil 1210, which can work with the ICE-LC moisture sensor 1215 when the reader coil 1210 is moved into a position to interrogate the ICE-LC moisture sensor 1215. With the bottom ICE coil 1219 and the resonant sensor 1205 are held in a fixed relative position to each other, positional independence is provided to use of the external reader 1209 and its reader coil 1210. The external reader 1209 can be coupled to a VNA, wired or wirelessly, to conduct automatic scans. The automatic scans can be performed periodically. FIG. 12B is a plot of the $|S_{11}|$ scattering parameter versus frequency that indicates decreasing of resonant frequency with increasing soil moisture.

Though the ICE-LC sensor of FIG. 12A is implemented as a moisture sensor, an ICE-LC sensor can be used to measure other properties. Variations of an ICE-LC sensor can be used in other measurement architectures in which monitoring a resonant sensor is performed with a non-fixed reader. The measurement arrangements are not limited to substantially vertical arrangements illustrated in FIG. 12A.

Figure 13:
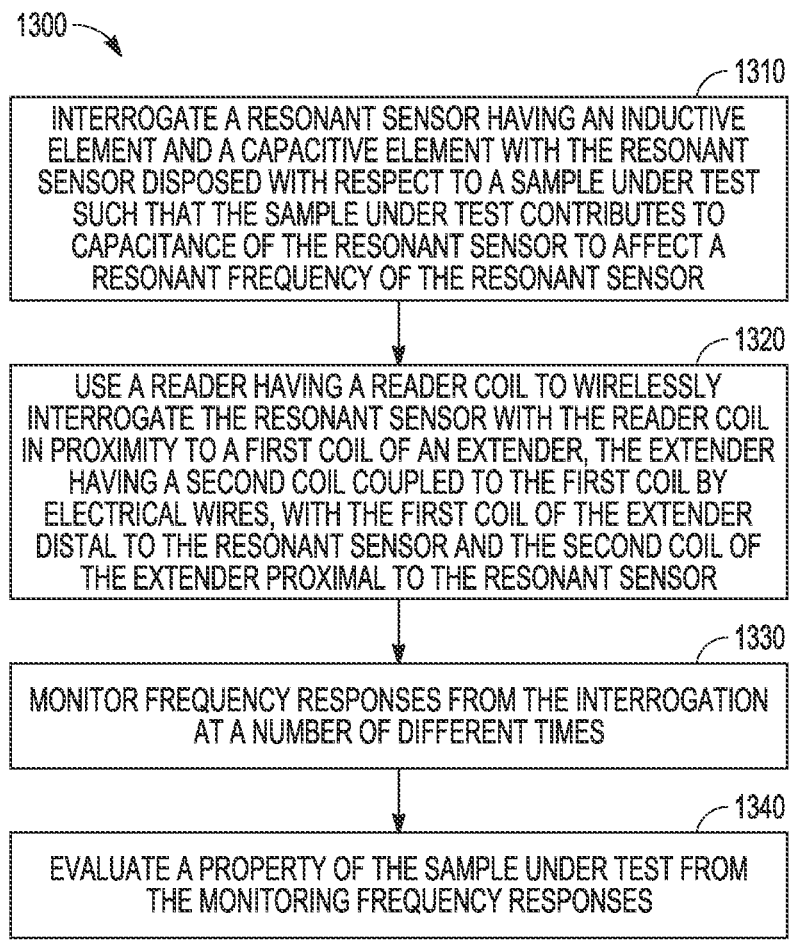
FIG. 13 is a flow diagram of features of an example method of measuring a sample, in accordance with various embodiments.

FIG. 13 is a flow diagram of features of a method 1300 of measuring a sample. Method 1300 can be a processor implemented method. At 1310, a resonant sensor having an inductive element and a capacitive element is interrogated. The resonant sensor can be disposed with respect to the sample under test such that the sample under test contributes to capacitance of the resonant sensor to affect a resonant frequency of the resonant sensor. The resonant sensor can be structured in a number of different formats. The resonant sensor can be rigid with the inductive element structured as an electrically conductive coil. The resonant sensor can be flexible with the inductive element structured as an electrically conductive coil on a polymer film. The capacitive element can include dielectric material between conductive lines of the electrically conductive coil. The electrically conductive coil of the resonant sensor can include, but is not limited to, copper.

At 1320, a reader having a reader coil to wirelessly interrogate the resonant sensor is used to perform the interrogating of the resonant sensor. The reader coil is disposed in proximity to a first coil of an extender, where the extender has a second coil coupled to the first coil by electrical wires forming a closed circuit. The first coil of the extender is distal to the resonant sensor and the second coil of the extender is proximal to the resonant sensor.

At 1330, frequency responses from the interrogation are monitored at a number of different times. At 1340, a property of the sample under test is evaluated from the monitoring of the frequency responses.

Variations of method 1300 or methods similar to method 1300 can include a number of different embodiments that can be combined depending on the application of such methods and/or the architecture of systems in which such methods are implemented. Such variations can include collecting scattering parameter data in the monitoring of the frequency responses. Such variations can include, in the evaluation of the property of the sample under test, comparing the monitored frequency responses to calibration data for a combination of the extender and resonate sensor associated with the sample under test. Method 1300 or variations thereof can implement one or more techniques associated with an ICE-LC sensor architecture taught herein.

In various embodiments, a machine-readable storage device, such as computer-readable medium, can comprise instructions stored thereon, which, when performed by a machine, cause the machine to perform operations. The instructions can be executed by one or more processors associated with the machine, where the operations comprise one or more features similar to or identical to features of methods and techniques described with respect to method 1300, variations thereof, and/or features of other methods taught herein such as associated with FIGS. 1-14. The physical structures of such instructions can be operated on by one or more processors. For example, executing these physical structures can cause the machine to perform operations comprising operations to: interrogate a resonant sensor having an inductive element and a capacitive element with the resonant sensor disposed with respect to a sample under test such that the sample under test contributes to capacitance of the resonant sensor to affect a resonant frequency of the resonant sensor; perform the interrogating of the resonant sensor using a reader having a reader coil to wirelessly interrogate the resonant sensor with the reader coil in proximity to a first coil of an extender, the extender having a second coil coupled to the first coil by electrical wires forming a closed circuit, with the first coil of the extender distal to the resonant sensor and the second coil of the extender proximal to the resonant sensor; monitor frequency responses from the interrogation at a number of different times; and evaluate a property of the sample under test from the monitoring of the frequency responses.

Operations can include collecting scattering parameter data in the monitoring of the frequency responses. Operations to evaluate a property of the sample under test can include comparing the monitored frequency responses to calibration data for a combination of the extender and resonate sensor associated with the sample under test. For a sensor system implemented for soil measurements, the calibration data of the combination of the extender and the resonant sensor can include calibration data correlated to soil moisture.

Further, machine-readable storage devices, such as computer-readable non-transitory media, herein, are physical devices that store data represented by physical structure within the respective device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices. The machine-readable device can be a machine-readable medium structured as a memory system. The term memory system should be taken to include all forms of storage media, either in the form of a single medium (or device) or multiple media (or devices), in all forms. For example, such structures can be realized as centralized database(s), distributed database(s), associated caches, and servers; one or more storage devices, such as storage drives (including but not limited to electronic, magnetic, and optical drives and storage mechanisms), and one or more instances of memory devices or modules (whether main memory; cache storage, either internal or external to a processor; or buffers). Terms such as "memory," "memory system," "storage device," "machine-readable medium," and "machine-readable device," shall be taken to include any tangible non-transitory medium that is capable of storing a sequence of instructions for execution by the machine and that cause the machine to perform any one of the methodologies taught herein. The term "non-transitory" used in reference to a "machine-readable device," "medium," "storage medium," "device," or "storage device"

expressly includes all forms of storage drives (optical, magnetic, electrical, etc.) and all forms of memory devices (e.g., DRAM, Flash (of all storage designs), SRAM, MRAM, phase change, etc., as well as all other structures designed to store data of any type for later retrieval.

In various embodiments, an apparatus can include a first coil and a second coil separated from the first coil, where the second coil is coupled to the first coil by electrical wires, with the first coil and the second coil structured as a closed circuit. The second coil can be separate from the first coil in an arrangement that is substantially a vertical configuration. The structure with the first coil coupled to the second coil by the electrical wires can be implemented without these components being directly connected to other electrical elements. Though the first coil and the second coil are arrangeable in a substantially vertical configuration, the first coil and the second coil can be arranged with other orientations depending on the application using the first coil and the second coil separated from each other, but coupled by electrical wires, forming a closed circuit. Such arrangements of the first coil and the second coil can be used as part of a sensor arrangement in which the electrically coupled first coil and second coil provide an extender circuit between components of a sensing system.

Variations of such an apparatus or similar apparatus can include a number of different embodiments that can be combined depending on the application of such apparatus and/or the architecture of systems in which such apparatus are implemented. Such variations can include the first coil or the second coil being a coil having one turn. The first coil or the second coil can be structured as a coil having multiple turns. The multiple turns can have a pitch in a range from approximately one millimeter to approximately ten millimeters. The multiple turns can have other pitch values depending on the application for which the first and second coils are structured.

Variations of such an apparatus or similar apparatus can include a support structure connecting the first coil to the second coil, with the electrical wires attached to the support structure. Variations can include the first coil and the second coil disposed on an electrically insulating sheet of material. The electrically insulating sheet of material can include, but is not limited to, a sheet of polyimide with the first coil, second coil, and the electrical wires coupling the first coil, to the second coil including copper.

In various embodiments, a sensor system can include a resonant sensor having a capacitive element and an inductive element and an extender, with the extender arrangeable alongside and separate from the resonant sensor. The resonant sensor can be disposed with respect to a sample under test such that the sample under test contributes to capacitance of the resonant sensor to affect a resonant frequency of the resonant sensor. The resonant sensor can be rigid with the inductive element structured as an electrically conductive coil. The resonant sensor can be flexible with the inductive element structured as an electrically conductive coil on a polymer film. The capacitive element can include dielectric material between conductive lines of the electrically conductive coil. The electrically conductive coil can include, but is not limited to, copper.

The extender can include a first coil and a second coil, where the second coil is separated from the first coil and is coupled to the first coil by electrical wires structured as a closed circuit. The first coil and the second coil can be arrangeable in a substantially vertical configuration. The structure with the first coil coupled to the second coil by the electrical wires can be implemented without these components being directly connected to other electrical elements. Though the first coil and the second coil are arrangeable in a substantially vertical configuration, the first coil and the second coil can be arranged with other orientations depending on the application using the first coil and the second coil separated from each other, but coupled by electrical wires, forming a closed circuit. Such arrangements of the first coil and the second coil in the sensor system can provide an extender circuit between the resonant sensor and a reader used in interrogation of the resonant sensor.

Such a sensor system can include a reader having a reader coil to wirelessly interrogate the resonant sensor with the reader coil in proximity to the first coil of the extender. In such an arrangement, the first coil of the extender can be distal to the resonant sensor and the second coil of the extender can be proximal to the resonant sensor. The reader can be movable to align the reader coil of the reader with the first coil, where the alignment is based on acceptable power transfer for conducting the measurements.

Variations of such a sensor system or similar sensor systems can include a number of different embodiments that can be combined depending on the application of such sensor systems and/or the architecture in which such sensor systems are implemented. Such variations can include the sensor system having a network analyzer coupled to the reader coil and arranged to collect scattering parameter data from interrogation of the resonant sensor. The network analyzer can be a vector network analyzer. Variations of such sensor systems can include the network analyzer wirelessly coupled to the reader.

Variations of such a sensor system or similar sensor systems can include a memory system and one or more processors configured to execute instructions stored on one or more components in the sensor system. The stored instructions, when executed by the one or more processors, can cause the sensor system to perform operations. The operations can include, but are not limited to, operations to analyze scattering parameter data operatively collected by the network analyzer and to determine one or more properties of a sample under test by the resonant sensor. The operations can include use of calibration data of a combination of the extender and the resonant sensor to determine the one or more properties of the sample under test. With the sensor system configured for soil measurements, the calibration data of the combination of the extender and the resonant sensor can be calibration data correlated to soil moisture. The sensor system can be configured for other measurements, with individual calibration data of the combination of the extender and the resonant sensor correlated to corresponding ones of the other measurements. The memory system and the one or more processors of the sensor system can be local to the network analyzer or remote from the network analyzer.

Figure 14:
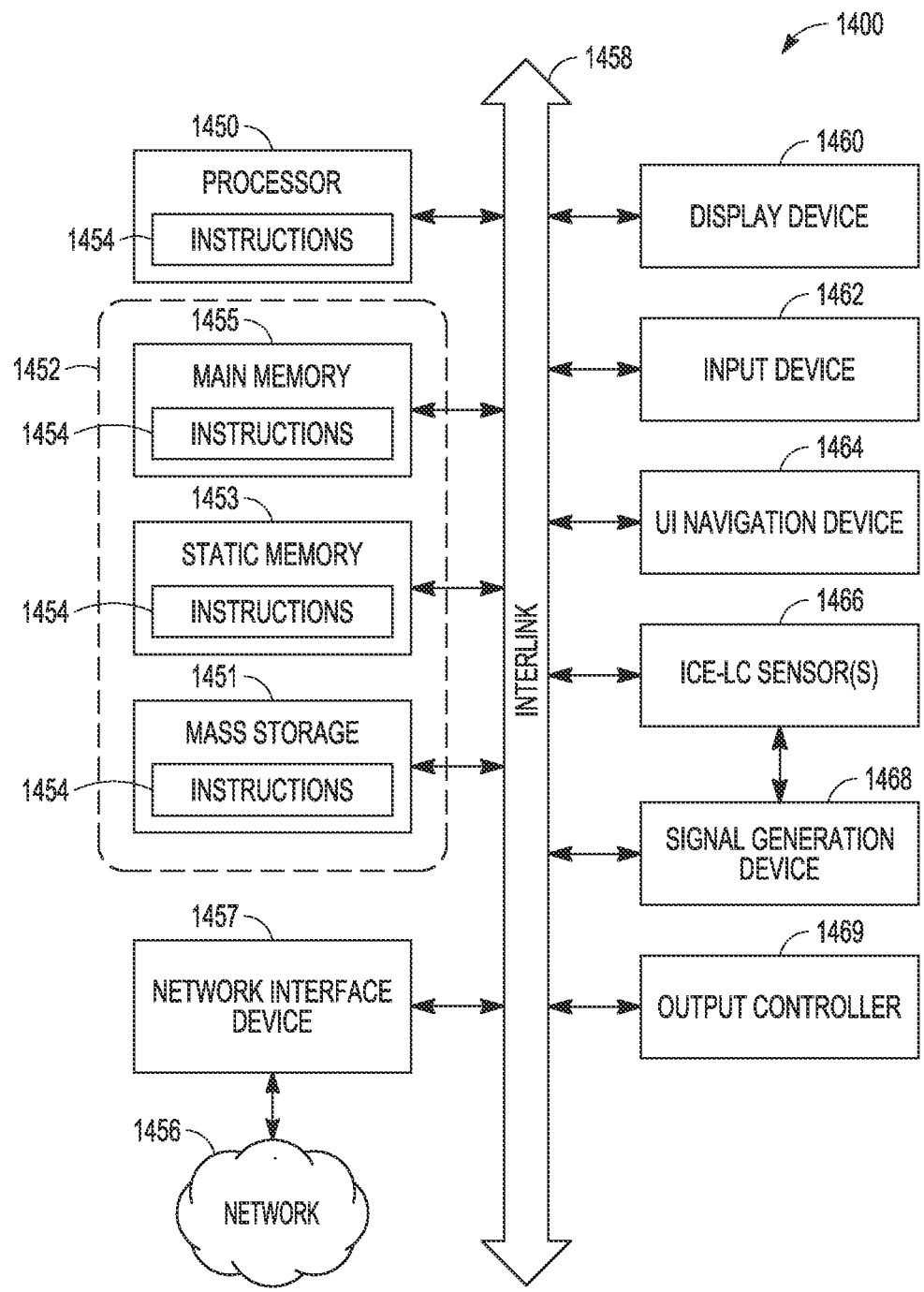
FIG. 14 is a block diagram illustrating components of an example system that can implement algorithms and perform methods structured to conduct measurements using an inductively coupled extender—inductive-capacitive sensor, in accordance with various embodiments.

FIG. 14 is a block diagram illustrating components of an embodiment of an example system 1400 that can implement algorithms and perform methods structured to conduct measurements using an ICE-LC sensor system, as taught herein. The system 1400 can include one or more processors 1450 that can be structured to execute stored instructions to perform functions to interrogate a resonant sensor of an ICE-LC sensor 1466, collect scattering data, analyze the collected scattering data, determine one or more properties of a sample being measured by the ICE-LC sensor 1466 in conjunction with a signal generation device 1468 that can include a reader device, and report out the results of the determinations. The system 1400 can include a number of ICE-LC sensors and signal generation devices 1468.

The system 1400 may operate as a standalone system or may be connected, for example networked, to other systems. In a networked deployment, the system 1400 can operate in the capacity of a server machine, a client machine, or both in server-client network environments. In an example, the system 1400 can act as a peer machine in peer-to-peer (P2P) (or other distributed) network environment. Further, while only a single system is illustrated, the term "system" shall also be taken to include any collection of systems that individually or jointly execute a set (or multiple sets) of instructions to perform any one or more of the methodologies discussed herein.

The machine (e.g., computer system) 1400 can include a hardware processor 1450 (e.g., a CPU, a GPU, a hardware processor core, or any combination thereof), a main memory 1455, and a static memory 1453, some or all of which can communicate with each other via components of an interlink (e.g., bus) 1458. The interlink 1458 can include a number of different communication mechanisms such as different wired communication mechanisms and different wireless communication mechanisms. The machine 1400 can further include a display device 1460, an alphanumeric input device 1462 (e.g., a keyboard), and a user interface (UI) navigation device 1464 (e.g., a mouse). In an example, the display device 1460, input device 1462, and UI navigation device 1464 can be a touch screen display. The machine 1400 can additionally include a mass storage device (e.g., drive unit) 1451, one or more signal generation devices 1468 that includes a reader to interrogate a resonant sensor of the one or more ICE-LC sensors 1466. The machine 1400 can include other sensors, such as a global positioning system (GPS) sensor, compass, accelerometer, or other communication-enabled sensors. The machine 1400 can include an output controller 1469, such as a serial (e.g., USB, parallel, or other wired or wireless (e.g., infrared (IR), near field communication (NFC), etc.) connection to communicate or control one or more peripheral devices (e.g., a printer, card reader, etc.).

The machine 1400 can include a machine-readable medium 1452 on which is stored one or more sets of data structures or instructions 1454 (e.g., software) embodying or utilized by the machine 1400 to perform any one or more of the techniques or functions for which the machine 1400 is designed. The instructions 1454 can also reside, completely or at least partially, within the main memory 1455, within static memory 1453, or within the hardware processor 1450 during execution thereof by the machine 1400. In an example, one or any combination of the hardware processor 1450, the main memory 1455, the static memory 1453, or the mass storage device 1451 can constitute the machine-readable medium 1452.

The instructions 1454 (e.g., software, programs, an operating system (OS), etc.) or other data are stored on the mass storage device 1451, can be accessed by the main memory 1455 for use by the processor 1450. The main memory 1455 (e.g., DRAM) is typically fast, but volatile, and thus a different type of storage than the mass storage device 1451 (e.g., an SSD), which is suitable for long-term storage, including while in an "off" condition. The instructions 1454 or data in use by a user or the machine 1400 are typically loaded in the main memory 1455 for use by the processor 1450. When the main memory 1455 is full, virtual space from the mass storage device 1451 can be allocated to supplement the main memory 1455; however, because the mass storage device 1451 is typically slower than the main memory 1455, and write speeds are typically at least twice as slow as read speeds, use of virtual memory can greatly reduce user experience due to storage device latency (in contrast to the main memory 1455, e.g., DRAM). Further, use of the mass storage device 1451 for virtual memory can greatly reduce the usable lifespan of the mass storage device 1451.

The instructions 1454, measurement data, or results of data analysis can further be transmitted or received over a communications network 1456 using a transmission medium via a network interface device 1457 utilizing any one of a number of transfer protocols (e.g., frame relay, Internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1457 can include one or more physical jacks (e.g., Ethernet, coaxial, or phone jacks) or one or more antennas to connect to the communications network 1456. In an example, the network interface device 1457 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any tangible medium that is capable of carrying instructions or data to and for execution by the machine 1400 and includes instrumentalities to propagate digital or analog communications signals to facilitate communication of such instructions, which instructions can be implemented by software, or data.

The following are example embodiments of methods, apparatus, and systems, in accordance with the teachings herein.

An example apparatus 1 can comprise: a first coil; and a second coil separated from the first coil and coupled to the first coil by electrical wires, with the first coil and the second coil structured as a closed circuit.

An example apparatus 2 can include elements of example apparatus 1, wherein the first coil or the second coil is a coil having one turn.

An example apparatus 3 can include elements of any preceding example apparatus, wherein the apparatus includes a support structure connecting the first coil to the second coil, with the electrical wires attached to the support structure.

An example apparatus 4 can include elements of any preceding example apparatus, wherein the first coil or the second coil is a coil having multiple turns.

An example apparatus 5 can include elements of example apparatus 4 and any preceding example apparatus, wherein the multiple turns have a pitch in a range from approximately one millimeter to approximately ten millimeters.

An example apparatus 6 can include elements of any preceding example apparatus, wherein the first coil and the second coil are disposed on an electrically insulating sheet of material.

An example apparatus 7 can include elements of example apparatus 6 and any preceding example apparatus, wherein the electrically insulating sheet of material includes a sheet of polyimide with the first coil, second coil, and the electrical wires coupling the first coil to the second coil including copper.

An example sensor system 1 can comprise an apparatus of any of the preceding example apparatus.

An example sensor system 2 can comprise: a resonant sensor having a capacitive element and an inductive element; and an extender, the extender arrangeable alongside and separate from the resonant sensor; the extender including: a first coil; and a second coil separated from the first coil and coupled to the first coil by electrical wires, with the first coil and the second coil structured as a closed circuit.

An example sensor system 3 can include elements of example system 2, wherein the resonant sensor is structured such that a sample under test by the resonant sensor contributes to capacitance of the resonant sensor to affect a resonant frequency of the resonant sensor.

An example sensor system 4 can include elements of any preceding example systems, wherein the sensor system includes a reader having a reader coil to wirelessly to interrogate the resonant sensor with the reader coil in proximity to the first coil of the extender, with the first coil of the extender distal to the resonant sensor and the second coil of the extender proximal to the resonant sensor.

An example sensor system 5 can include elements of example sensor system 4 and any preceding example systems, wherein the reader is movable to align the reader coil with the first coil.

An example sensor system 6 can include elements of example sensor system 4 and any preceding example systems, wherein the sensor system includes a network analyzer coupled to the reader coil and arranged to collect scattering parameter data from interrogation of the resonant sensor.

An example sensor system 7 can include elements of example sensor system 6 and any preceding example systems, wherein the network analyzer is a vector network analyzer.

An example sensor system 8 can include elements of example sensor system 6 and any preceding example systems, wherein the network analyzer is wirelessly coupled to the reader.

An example sensor system 9 can include elements of example sensor system 6 and any preceding example systems, wherein the sensor system includes: a memory system; and one or more processors configured to execute instructions stored on one or more components in the sensor system, which instructions, when executed by the one or more processors, cause the sensor system to perform operations to: analyze scattering parameter data operatively collected by the network analyzer; and determine one or more properties of a sample under test by the resonant sensor.

An example sensor system 10 can include elements of example sensor system 9 and any preceding example systems, wherein the operations include use of calibration data of a combination of the extender and the resonant sensor to determine the one or more properties of the sample under test.

An example sensor system 11 can include elements of example sensor system 10 and any preceding example systems, wherein the calibration data of the combination of the extender and the resonant sensor is calibration data correlated to soil moisture.

An example sensor system 12 can include elements of example sensor system 9 and any preceding example systems, wherein the memory system and the one or more processors are remote from the network analyzer.

An example method 1 can comprise operating any example apparatus 1-7.

An example method 2 can comprise forming any example apparatus 1-7.

An example method 3 can comprise operating any example sensor system 1-9.

An example method 4 can comprise forming any example sensor system 1-9.

An example method 5 can comprise: interrogating a resonant sensor having an inductive element and a capacitive element with the resonant sensor disposed with respect to a sample under test such that the sample under test contributes to capacitance of the resonant sensor to affect a resonant frequency of the resonant sensor; performing the interrogating of the resonant sensor using a reader having a reader coil to wirelessly interrogate the resonant sensor with the reader coil in proximity to a first coil of an extender, the extender having a second coil coupled to the first coil by electrical wires forming a closed circuit, with the first coil of the extender distal to the resonant sensor and the second coil of the extender proximal to the resonant sensor; monitoring frequency responses from the interrogation at a number of different times; and evaluating a property of the sample under test from the monitoring of the frequency responses.

An example method 6 can include elements of preceding example method 5, wherein monitoring the frequency responses includes collecting scattering parameter data.

An example method 7 can include elements of any preceding example methods 5 and 6, wherein evaluating a property of the sample under test includes comparing the monitored frequency responses to calibration data for a combination of the extender and resonate sensor associated with the sample under test.

An example machine-readable storage device comprising instructions, which, when executed by a set of processors, cause a system to perform operations, the operations comprising operations to perform elements of any of example methods 1-7.

An example method 9 can comprise: forming a resonant sensor having an inductive element and a capacitive element; and forming an extender including: a first coil; and a second coil separated from the first coil and coupled to the first coil by electrical wires, with the first coil and the second coil structured as a closed circuit.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description.

What is claimed is:

1. An apparatus comprising:
   a first coil;
   a second coil separated from the first coil and coupled to the first coil by electrical wires, with the first coil and the second coil structured as a closed circuit and with the electrical wires in polymer sleeves;
   a resonant sensor operable to measure a property of a sample, the resonant sensor arranged in a fixed position relative to the first coil and separated from the first coil by non-conductive material, the resonant sensor having a capacitive element and an inductive element, the capacitive element structured within the inductive element and having dielectric material between and contacting conductive lines of the inductive element; and a storage component having calibration data of a combination of the resonant sensor with the first coil and the second coil being calibrated with respect to the sample.

2. The apparatus of claim 1, wherein the first coil or the second coil is a coil having one turn.

3. The apparatus of claim 1, wherein the apparatus includes a support structure connecting the first coil to the second coil, with the electrical wires attached to the support structure.

4. The apparatus of claim 1, wherein the first coil or the second coil is a coil having multiple turns.

5. The apparatus of claim 4, wherein the multiple turns have a pitch in a range from approximately one millimeter to approximately ten millimeters.

6. The apparatus of claim 1, wherein the first coil and the second coil are disposed on an electrically insulating sheet of material.

7. The apparatus of claim 6, wherein the electrically insulating sheet of material includes a sheet of polyimide with the first coil, second coil, and the electrical wires coupling the first coil to the second coil including copper.

8. A sensor system comprising:
a resonant sensor operable to measure a property of a sample under test, the resonant sensor being a passive sensor having a capacitive element and an inductive element, with the capacitive element being a dielectric within a structure of the inductive element such that the dielectric is between and contacting conductive lines of the inductive element;
an extender arrangeable alongside and separate from the resonant sensor;
the extender including;
a first coil; and
a second coil separated from the first coil and coupled to the first coil by electrical wires, with the first coil and the second coil structured as a closed circuit, with the second coil arranged in a fixed position relative to the resonant sensor and separated from the resonant sensor by non-conductive material; and
a storage component having calibration data of a combination of the resonant sensor with the first coil and the second coil being calibrated with respect to the sample under test.

9. The sensor system of claim 8, wherein the resonant sensor is structured such that a sample under test by the resonant sensor contributes to capacitance of the resonant sensor to affect a resonant frequency of the resonant sensor.

10. The sensor system of claim 8, wherein the sensor system includes a reader having a reader coil to wirelessly interrogate the resonant sensor with the reader coil in proximity to the first coil of the extender, with the first coil of the extender distal to the resonant sensor and the second coil of the extender proximal to the resonant sensor.

11. The sensor system of claim 10, wherein the reader is movable to align the reader coil with the first coil.

12. The sensor system of claim 10, wherein the sensor system includes a network analyzer coupled to the reader coil and arranged to collect scattering parameter data from interrogation of the resonant sensor.

13. The sensor system of claim 12, wherein the network analyzer is a vector network analyzer.

14. The sensor system of claim 12, wherein the network analyzer is wirelessly coupled to the reader.

15. The sensor system of claim 12, wherein the sensor system includes:
a memory system; and
one or more processors configured to execute instructions stored on one or more components in the sensor system, which instructions, when executed by the one or more processors, cause the sensor system to perform operations to:
analyze scattering parameter data operatively collected by the network analyzer; and
determine one or more properties of the sample under test by the resonant sensor.

16. The sensor system of claim 15, wherein the operations include use of the calibration data of the combination of the extender and the resonant sensor to determine the one or more properties of the sample under test.

17. The sensor system of claim 16, wherein the calibration data of the combination of the extender and the resonant sensor is calibration data correlated to soil moisture.

18. The sensor system of claim 15, wherein the memory system and the one or more processors are remote from the network analyzer.

19. A method comprising:
interrogating a resonant sensor having an inductive element and a capacitive element, with the resonant sensor disposed with respect to a sample under test such that the sample under test contributes to capacitance of the resonant sensor to affect a resonant frequency of the resonant sensor;
performing the interrogating of the resonant sensor using a reader having a reader coil to wirelessly interrogate the resonant sensor with the reader coil in proximity to a first coil of an extender, the extender having a second coil coupled to the first coil by electrical wires forming a closed circuit, with the first coil of the extender distal to the resonant sensor and the second coil of the extender proximal to the resonant sensor;
monitoring frequency responses from the interrogation at a number of different times; and
evaluating a property of the sample under test from the monitoring of the frequency responses, including comparing the monitored frequency responses to calibration data for a combination of the extender and resonant sensor associated with the sample under test.

20. The method of claim 19, wherein monitoring the frequency responses includes collecting scattering parameter data.

21. The method of claim 19, wherein the sample under test is in an underground environment, and evaluating the property of the sample under test is based on relative permittivity of the sample under test or the underground environment about the sample under test.

* * * * *

UNITED STATES PATENT AND TRADEMARK OFFICE
CERTIFICATE OF CORRECTION

| | |
|---|---|
| PATENT NO. | : 12,313,581 B2 |
| APPLICATION NO. | : 17/820753 |
| DATED | : May 27, 2025 |
| INVENTOR(S) | : Chan et al. |

Page 1 of 1

It is certified that error appears in the above-identified patent and that said Letters Patent is hereby corrected as shown below:

In the Specification

In Column 6, Line 22, delete "1119," and insert --119,-- therefor

In Column 6, Line 25, delete "115," and insert --105,-- therefor

In Column 6, Line 27, delete "115," and insert --105,-- therefor

In Column 6, Lines 47-48, delete "IS 11" and insert --$|S_{11}|$-- therefor

In Column 12, Line 44, delete "A" and insert --$\Delta$-- therefor

Signed and Sealed this
Fifth Day of August, 2025

Coke Morgan Stewart
*Acting Director of the United States Patent and Trademark Office*